US007858123B2

(12) United States Patent
Stucky et al.

(10) Patent No.: US 7,858,123 B2
(45) Date of Patent: Dec. 28, 2010

(54) INORGANIC MATERIALS FOR HEMOSTATIC MODULATION AND THERAPEUTIC WOUND HEALING

(75) Inventors: Galen D. Stucky, Santa Barbara, CA (US); Todd A. Ostomel, Santa Barbara, CA (US); Qihui Shi, Goleta, CA (US); Peter K. Stoimenov, Goleta, CA (US); Patricia A. Holden, Santa Barbara, CA (US)

(73) Assignee: The Regents of the University of California, Oakland, CA (US)

( * ) Notice: Subject to any disclaimer, the term of this patent is extended or adjusted under 35 U.S.C. 154(b) by 188 days.

(21) Appl. No.: 11/398,161

(22) Filed: Apr. 4, 2006

(65) Prior Publication Data

US 2007/0031515 A1 Feb. 8, 2007

Related U.S. Application Data

(60) Provisional application No. 60/668,022, filed on Apr. 4, 2005.

(51) Int. Cl.
*A61K 9/14* (2006.01)
*A61K 33/00* (2006.01)
*A61K 47/00* (2006.01)
*A01N 59/00* (2006.01)
*A01N 25/00* (2006.01)
*A61M 1/00* (2006.01)

(52) U.S. Cl. .................. 424/600; 424/489; 424/617; 424/618; 514/769; 514/770; 604/367

(58) Field of Classification Search ........... 424/489, 424/600, 617, 618; 514/769, 770; 604/367; 128/156
See application file for complete search history.

(56) References Cited

U.S. PATENT DOCUMENTS

| | | | | |
|---|---|---|---|---|
| 2,882,243 | A | * | 4/1959 | Milton ................. 423/718 |
| 3,723,352 | A | * | 3/1973 | Warner et al. ............ 502/60 |
| 4,626,550 | A | * | 12/1986 | Hertzenberg ............. 514/770 |
| 4,744,805 | A | * | 5/1988 | Maroulis et al. ............ 95/82 |
| 4,748,978 | A | | 6/1988 | Kamp |
| 4,822,349 | A | | 4/1989 | Hursey |
| 5,436,362 | A | * | 7/1995 | Kondoh et al. ............ 558/277 |
| 6,767,550 | B1 | | 7/2004 | Genin |
| 2003/0133990 | A1 | | 7/2003 | Hursey et al. |
| 2003/0198660 | A1 | | 10/2003 | Janas |
| 2004/0043053 | A1 | | 3/2004 | Yu |
| 2005/0058721 | A1 | | 3/2005 | Hursey |
| 2005/0065214 | A1 | | 3/2005 | Kronenthal |
| 2005/0074505 | A1 | | 4/2005 | Hursey |
| 2007/0154509 | A1 | | 7/2007 | Wilcher et al. |
| 2007/0154510 | A1 | | 7/2007 | Wilcher et al. |
| 2007/0154564 | A1 | | 7/2007 | Stucky et al. |
| 2008/0125686 | A1 | | 5/2008 | Lo |
| 2008/0145455 | A1 | | 6/2008 | Bedard |

FOREIGN PATENT DOCUMENTS

| | | |
|---|---|---|
| CN | 1727011 A | 1/2006 |
| JP | 3272770 | 4/1991 |
| WO | WO/97/17401 | 5/1997 |
| WO | WO/98/47465 | 10/1998 |
| WO | WO/00/76486 | 12/2000 |
| WO | WO/2004/071542 | 8/2004 |
| WO | WO 2005/027808 A1 | 3/2005 |
| WO | WO/2005/027808 A1 | 3/2005 |
| WO | WO/2006/012218 A1 | 2/2006 |
| WO | WO 2006088912 | 8/2006 |
| WO | WO 2006110393 | 10/2006 |
| WO | WO 2007022264 | 2/2007 |

OTHER PUBLICATIONS

Raymond Le Van Mao, Mesoporous Aluminosilicates prepared from Zeolites by Treatment with Ammonium Fluorosilicate, 1993, J. Mater. Chem., 3(6), pp. 679-683.*
Dyer and Faghihian. Diffusion in heteroionic zeolites: part 1. Diffusion of water in heteroionic natrolites. Elservier, Microporous and Mesoporous Materials 1998, 21, pp. 27-28.
Top and Ülkü. Silver, zinc, and copper exchange in a Na-clinoptilolite and resulting effect on antibacterial activity, Elsevier, Science Direct, Applied Clay Science, 2004, 27, pp. 13-19.
Dyer, A., et al. Diffusion in heteroionic zeolites: part 1—Diffusion of water in heteroionic natrolites. Microporuous and Mesoporous Materials. 1998, vol. 21, pp. 27-38.
Top, A., et al. Silver, zinc, and copper exchange in a Na-clinoptilolite and resulting effect on antibacterial activity. Applied Clay Science. 2004, vol. 27, pp. 13-19.
Wright, J. K., et al. Thermal injury resulting from application of a granular mineral hemostatic agent. The Journal of Trauma Injury, Infection and Critical Care. 2004, vol. 57, No. 2, pp. 224-230.
Abe, Y., et al. Effect of saliva on an antimicrobial tissue conditioner containing silver-zeolite. Journal of Oral Rehabilitation. 2004, vol. 31, pp. 568-573.
Acheson, E., et al. Comparison of hemorrhage control agents applied to lethal extremity arterial hemorrhages in swine. Journal of Trauma Injury, Infection and Critical Care. 2005, vol. 59, pp. 865-875.
Ahuja, N., et al. Testing of modified zeolite hemostatic dressings in a large animal model of lethal groin injury. Journal of Trauma Injury, Infection and Critical Care. 2006, vol. 61, pp. 1312-1320.

(Continued)

*Primary Examiner*—Johann R Richter
*Assistant Examiner*—Luke E Karpinski
(74) *Attorney, Agent, or Firm*—Rudy J. Ng; Carol L. Francis; Bozicevic, Field & Francis, LLP

(57) ABSTRACT

The invention provides compositions, methods and devices relating to a silaceous oxide that generates a reduced heat of hydration upon contact with blood. By reducing the heat of hydration, the compositions provide a hemostatic agent that attenuates a tissue burning side effect of conventional hemostatic agents without adversely affecting the wound healing properties of the composition.

20 Claims, 21 Drawing Sheets

OTHER PUBLICATIONS

Alam, H., et al. Comparative analysis of hemostatic agents in a swine model of lethal groin injury. Journal of Trauma Injury, Infection and Critical Care. 2003, vol. 54, pp. 1077-1082.

Alam, H. et al. Application of a zeolite hemostatic agent achieves 100% survival in a lethal model of complex groin injury in swine. Journal of Trauma Injury, Infection and Critical Care. 2004, vol. 56, pp. 974-983.

Alam, H., et al. Hemorrhage control in the battlefield: role of new hemostatic agents. Military Medicine. 2005, vol. 170, pp. 63-69.

Browne, J., et al. Characterization and adsorptive properties of pharmaceutical grade clays. Journal of Pharmaceutical Sciences. 1980, vol. 69, No. 7, pp. 816-823.

Davie, E., et al. The coagulation cascade: initiation, maintenance and regulation. Biochemistry. 1991, vol. 30, No. 43, pp. 10363-10370.

Drebushchak, V., et al. Measurements of heat of zeolite dehydration by scanning heating. Journal of Thermal Analysis and Calorimetry. 1999, vol. 58, pp. 653-662.

Hench, L., et al. Bioceramics. Journal of the American Ceramic Society. 1998, vol. 81, No. 7, pp. 1705-1728.

Hoffman, M., et al. Remodeling the blood coagulation cascade. Journal of Thrombosis and Thrombolysis. 2003, vol. 16, pp. 17-20.

Huo, Q., et al. Generalized synthesis of periodic surfactant/inorganic composite materials. Nature. 1994, vol. 368, pp. 317-321.

Jalilehvand, F., et al. Hydration of the calcium ion. An EXAFS, large-angle x-ray scattering, and molecular dynamics simulation study. Journal of the American Chemical Society. 2001, vol. 123, pp. 431-441.

Kawahara, K., et al. Antibacterial effect of silver-zeolite on oral bacteria under anaerobic conditions. Dental Materials. 2000, vol. 16, pp. 452-455.

Kheirabadi, B., et al. Hemostatic efficacy of two advanced dressing in an aortic hemorrhage model in swine. Journal of Trauma Injury, Infection and Critical Care. 2005, vol. 59, pp. 25-35.

Koper, O., et al. Alkaline-earth oxide nanoparticles obtained in aerogel methods. Characterization and rational for unexpectedly high surface chemical reactivities. Chemistry of Materials. 1997, vol. 9, pp. 2468-2480.

Lu, H., et al. Surface characterization of hydroxyapatite and related calcium phosphates by XPS and TOF-SIMS. Analytical Chemistry. 2000, vol. 72, pp. 2886-2894.

Mizota, T., et al. Hydration enthalpies of synthetic Na-A, cation-exchanged-A and some natural zeolites for evaluating as heat exchange absorbents. Thermochimica Acta. 1995, vol. 266, pp. 331-341.

Ostomel, T., et al. Host-guest composites for induced hemostasis and therapeutic healing in traumatic injuries. Journal of thrombosis and thrombolysis. 2006, vol. 22, pp. 55-67.

Ostomel, T., et al. Oxide hemostatic activity. Journal of the American Chemical Society. 2006, vol. 128, pp. 8384-8385.

Ostomel, T., et al. Spherical bioactive glass with enhanced rates of hydroxyapatite deposition and hemostatic activity. Small. 2006, vol. 2, No. 11, pp. 1261-1265.

Perez-Pariente, J., et al. Surface and chemical study of $SiO_2$-$P_2O_5$-CaO-(MgO) Bioactive Glasses. Chemistry of Materials. 2000, vol. 12, pp. 750-755.

Portier, J., et al. Acid-base behavior of oxides and their electronic structure. Solid State Sciences. 2003, vol. 5, pp. 695-699.

Sekiyah, F., et al. Magnesium (II) is a crucial constituent of the blood coagulation cascade. Journal of Biological Chemistry. 1996, vol. 271, No. 15, pp. 8541-8544.

Shimojima, A., et al. Direct formation of mesostructured silica-based hybrids from novel siloxane oligomers with long alkyl chains. Angewandte Chemie. 2003, vol. 42, pp. 4057-4060.

Wolberg, A., et al. A systematic evaluation of the effect of temperature on coagulation enzyme activity and platelet function. Journal of Trauma Injury, Infection and Critical Care. 2004, vol. 56, pp. 1221-1228.

Yang, Y., et al. H NMR spectroscopic evidence of interaction between ibuprofen and lipoproteins in human blood plasma. Analytical Biochemistry. 2004, vol. 324, pp. 292-297.

Yu, B., et al. A thermoanalytical study of dehydration and NaA, MgNaA and SrNaA zeolites. Thermochimica Acta. 1992, vol. 200, pp. 299-308.

Zhao, D., et al. Nonionic triblock and star diblock copolymer and oligomeric surfactant syntheses of highly ordered, hydrothermally stable, mesoporous silica structures. Journal of the American Chemical Society. 1998, vol. 120, pp. 6024-6036.

Breck, D., et al. Crystalline zeolites. I. The properties of a new synthetic zeolite, type A. Journal of the American Chemical Society. 1956, vol. 78, No. 23, pp. 5963-5972.

Hench, L., et al. Bonding mechanisms at the interface of ceramic prosthetic materials. J Biomed Mater Res Symposium. 1971, No. 2, pp. 117-141.

Mineral Herbal Medicine, edited by Lanzhong Guo, 1995, pp. 59-61.

Wright, James K., et al., "Thermal Injury Resulting from Application of a Granular Mineral Hemostatic Agent", Aug. 2004, The Journal of Trauma, 57(2).

Saravanapavan, P., et al., "Low-temperature Synthesis, Structure, and Bioactivity of Gel-derived . . . system", Mar. 2001, J. Biomed Mater Res., 54(4):608-18 (1pg Abstract only).

Sepulveda, Pilar, et al., "Bioactive Sol-gel Foams for Tissue Repair", Center for Tissue Engineering and Repair, London/UK, John Wiley & Sons, Inc. Jun. 2001, p. 340-348.

* cited by examiner

INORGANIC MATERIALS FOR HEMOSTATIC MODULATION AND THERAPEUTIC WOUND HEALING

This application claims the benefit of U.S. provisional patent application Ser. No. 60/668,022, filed Apr. 4, 2005, the entire contents of which are incorporated herein by reference.

GOVERNMENT RIGHTS

This invention was made with Government support under Grant No. N00014-04-1-0654, awarded by the Office of Naval Research. The Government has certain rights in this invention.

TECHNICAL FIELD OF THE INVENTION

The invention disclosed herein relates to compositions and methods for modulating the blood coagulation cascade, reducing the risk of microbial infection and promoting bone growth. Porous and nonporous high surface area small particle inorganic materials have been designed to treat traumatically injured tissue through rapid dehydration of a wound, promotion of blood clot formation, ion exchange with the tissue media for antibiotic and therapeutic activity, and controllable warming of the injured site.

BACKGROUND OF THE INVENTION

U.S. Pat. No. 4,822,349 issued to Hursey, et. al. describes reduction of blood flow by application of a dehydrated zeolite material to the site of blood flow. In this method, a particular calcium rich zeolite formulation of the class Linde Type 5A has been utilized as an external application to a traumatically wounded individual to induce haemostasis through dehydration of the wounded area and induction of a blood clot formation (Breck, D W et al., *J An. Chem. Soc.* 78, 23 (1956) 5963.). A major disadvantage to this product has been the excessive heat generated locally at the injured site as a consequence of the large enthalpy of hydration associated with the material currently marketed under the trade name, Quik-Clot® and distributed by Z-medica corporation of Wallingford, Conn. USA. There remains a need for modifications and improvements that minimize the enthalpy of hydration upon rehydration of the dehydrated zeolite.

SUMMARY OF THE INVENTION

The invention provides a composition comprising a hemostatically effective amount of a silaceous oxide that generates a reduced heat of hydration upon contact with blood. Typically the silaceous oxide is negatively charged. By reducing the heat of hydration, the compositions attenuate a tissue burning side effect of conventional hemostatic agents without adversely affecting the wound healing properties of the composition. In one example of a composition of the invention, the heat of hydration is not greater than 125° C., or not greater than 175° C., as determined by thermal imaging, or not greater than 680 J/g, or not greater than 660 J/g, as determined by differential scanning calorimetry (DSC), upon contact with blood. In one embodiment, the heat of hydration is not greater than 67° C., as determined by thermal imaging. In another example, the silaceous oxide generates a heat of hydration of between 100 J/g and 650 J/g.

The silaceous oxide is typically selected from the group consisting of: glass beads, ceramics, silicates, aluminosilicates, aluminophosphates, diatomaceous earth, bioactive glass, borosilicate bioactive glass, titania and alumina; and optionally, pyrex or quartz. The silaceous oxide can be a zeolite, alone or in combination with another silaceous oxide. The glass or ceramic beads can be from about 10 nm to about 100 μm in diameter, or from about 100 nm to about 100 μm, and in some embodiments, the beads are about 50-200 nm in diameter. The silaceous oxide can have a range of porosities, including, but not limited to, a mesoporous silicate having pores of 2-50 nm diameter, a microporous (or sub-microporous) silicate having pores of 50-100 nm diameter, a macroporous silicate having pores of 100-200 μm diameter, or a nonporous silaceous oxide.

The composition optionally further comprises an inorganic salt, such as a divalent cation, examples of which include, but are not limited to, zinc, copper, magnesium, calcium and nickel. Representative inorganic salts include, but are not limited to, $CaO$, $CaCl_2$, $AgNO_3$, $Ca(NO_3)_2$, $Mg(NO_3)_2$, $Zn(NO_3)_2$, $NH_4NO_3$, $AgCl$, $Ag_2O$, zinc acetate, magnesium acetate, calcium citrate, zinc citrate, magnesium citrate, calcium acetate and calcium phosphate. In one embodiment, the $AgNO_3$ is provided via ion exchange, typically with a minimal loading of $Ag^+$ of about 0.2 atomic % as determined by X-ray photoelectron spectroscopy. In another embodiment, the $AgNO_3$ is provided via solid state mixing, typically with a minimal loading of $AgNO_3$ of about 0.01% by weight.

The composition can comprise an aluminosilicate that has a ratio of silicon to aluminum of 1.01 or greater, 32 to 1 or greater, or, in some embodiments, 100 to 1 or greater, or 1000 to 1 or greater. Another means of reducing the heat of hydration involves providing a composition wherein the silaceous oxide is hydrated to between 0.1% and 25%, between 0.1% and 5% by weight, or typically, between 1% and 5% by weight. In one embodiment, the silaceous oxide has an internal surface area of between 1 and 1000, or up to 1500 square meters per gram as determined by BET $N_2$ adsorption.

The invention further provides a method of producing a composition for modulating hemostasis, and also a method of modulating hemostasis comprising contacting blood with a composition of the invention. In some embodiments, the modulating comprises decreasing blood coagulation time. In one embodiment, the time to initiate coagulation (R), as measured by thromboelastograph®, is less than 2 minutes. In another embodiment, the rate of coagulation (α), as measured by thromboelastograph®, is greater than 50°, or greater than 65°. In a further embodiment, the coagulation results in a maximum clot strength (MA), as measured by thromboelastograph®, of greater than 55 mm, typically between about 65 and 80 mm. Alternatively, the modulating comprises increasing, rather than decreasing, blood coagulation time.

The modulation of hemostasis can be applied to a variety of circumstances in which control of hemostasis, to increase or decrease coagulation time, is desired. For example, accelerating coagulation is desirable in wound repair and surgical settings to avoid excessive blood loss. In other contexts, however, reduced coagulation is desired to avoid thrombosis. One example of an environment in which control of hemostasis is desired is that of an extracorporeal circuit or other blood-contacting device.

Also provided is a medical device that has been coated with the composition of the invention. Coatings can be prepared from a composition in powder form or using sol-gel chemistry, doctor-blading and calcination, aerosol spraying, dip-coating, and/or spin-casting.

DETAILED DESCRIPTION OF THE INVENTION

Figure 1A:
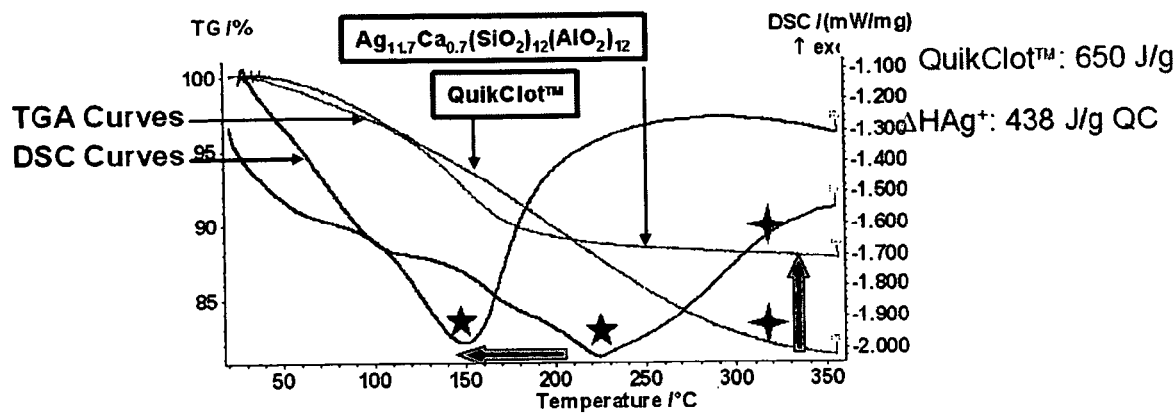
FIG. 1A shows the results of Differential Scanning Calorimetry (DSC) and Thermogravimetric Analysis (TGA) of QuikClot® and a silver ion exchanged formulation.

The invention is based on the discovery that it is possible to control the amount of heat released by hemostatic agents by modifying the hydration and/or ion content of the inorganic materials. In addition, one can modify the coagulation and anticoagulation effected by the materials to suit the objective in a particular application. The invention further provides alternative means for preparing a composition to adapt its use for different environments, such as surgery or trauma.

The inorganic materials comprise silaceous oxides, such as zeolites, molecular sieves, ceramics, nanoceramics, mesoporous silicates and inorganic salts mixed together in a dehydrated state, which can then be sealed in mylar foil bags prior to medical application. The size of the particles, the pore architecture, hydration status, acid-base properties, pore dimensions, and surface area can be synthetically tuned for each material for use as a hemostatic agent. Combinations of particular ceramics and oxides and of particular dimensions can be fabricated to modulate various pathways of the blood coagulation cascade. The hemostatic agents described herein are capable of immobilizing components of blood, concentrating blood clotting factors, controlling the local electrolyte concentration, and applying a predictable amount of heat to an injured site.

Many of the exemplary embodiments described herein use zeolites. It is understood that other silaceous oxides can be used as a molecular sieve in place of or together with a zeolite. Some examples of such alternative embodiments are described in greater detail below.

Definitions

All scientific and technical terms used in this application have meanings commonly used in the art unless otherwise specified. As used in this application, the following words or phrases have the meanings specified.

As used herein, a "hemostatically effective amount" means an amount sufficient to initiate detectable blood clotting (R) within 2 minutes, and/or achieve a rate of clotting ($\alpha$) of 50° or greater, and/or achieve a clot strength (MA) of $\geq$50, as determined by Thromboelastograph®. Assays for determining hemostatic effectiveness are known in the art, and described in the Examples below.

As used herein, a "thromboelastograph" assay refers to measurements typically taken using about 5-30 mg of material mixed with 340 microliters of citrate stabilized blood. Calcium ions are re-supplied to the citrate stabilized blood prior to measurements to replace the calcium ions chelated by citrate.

As used herein, "differential scanning calorimetry" or "DSC" is performed by first hydrating the material in an enclosed container with a saturated aqueous solution of KBr to maintain a humidity of 80%. The DSC response associated with desorbing that water from the saturated material as a function of temperature is then measured. The total "heat of hydration" is calculated by integrating the DSC response over the temperature range of desorption of water.

As used herein, "a" or "an" means at least one, unless clearly indicated otherwise.

Overview of Zeolite-Based Embodiments

Zeolites are high surface area porous aluminosilicates. The oxide structural framework is built up from tetrahedral units of $SiO_4$ and $AlO_4$ linked together through shared oxygen atoms. Each Al position in the oxide framework induces a negative charge that can be counterbalanced by counter-cations that reside in the open porous network coulombically bound to the oxide framework. When zeolites are extensively dehydrated, they are capable of rapidly absorbing water up to 30% by weight. Rehydration of a zeolite is an exothermic, or heat releasing reaction, and can predictability warm a known volume of liquid. Additionally, zeolites have an added property that allows for ionic exchange of the zeolite's cations with a solution in contact with the zeolite. In part due to some of these listed properties, the zeolite Linde type A discussed in this disclosure also has the ability to induce a blood clot in hemorrhaging blood and temporarily stabilize a patient that might otherwise have died as a result of exsanguination.

In one embodiment, the invention provides a calcium loaded zeolite IIinde type A that is ion exchanged with an aqueous solution of alkali, alkaline earth, and/or transition metal cations to specific ion formulations. This ion exchanged zeolite can be mixed with neutral inorganic salts like calcium chloride, aluminum sulfate, and silver nitrate and dehydrated to remove water. The dehydrated inorganic materials can be sealed in mylar foil bags to prevent rehydration until their use is required during medical application. At the time of medical application, the mylar bag can be opened and the inorganic contents poured into the traumatically injured site.

Three different modifications to zeolite (QuikClot®) are described in the following. Each modification offers advantages for a particular application.

1. Ion Exchanging Zeolite: QuikClot®, prepared with calcium as the major cation present, is ion exchanged with aqueous solutions of alkali, alkaline earth, and transition metals. This is accomplished by immersing QuikClot® in 0.1 M to 1 M aqueous solutions of lithium chloride, sodium chloride, potassium chloride, strontium nitrate, barium nitrate, ammonium chloride, or silver nitrate for three thirty minute intervals. The exchanging solution is removed in between each successive washing. Three final rinses with dionized water complete the removal of any soluble ions not incorporated with the zeolite material. The ion exchanged material is heated to at least 100° C. under vacuum ($10^{-3}$ torr) for 12 hours to remove water bound inside the zeolite. The material is then sealed in a mylar foil bag until medical application.

2. Composites of Zeolite with inorganic salts: Composites consisting of QuikClot® and inorganic salts including but not limited to calcium chloride, aluminum sulfate, and silver nitrate are blended together in a dehydrated state. These inorganic salts.can comprise between 0.001% and 50% by weight of the composite. The composites are heated to at least 100° C. under vacuum ($10^{-3}$ torr) for 12 hours to remove water bound inside the zeolite. The material is then sealed in a mylar foil bag until medical application.

3. Partial Hydration of Zeolite: Partially prehydrating QuikClot® can significantly reduce the total enthalpy of rehydration. QuikClot® can be stored from 1 day to two weeks in a humidity chamber regulated at 0 to 80% natural humidity relative to pure phase water. The extent of hydration is controlled by the duration and humidity setting of the storage conditions. The partially hydrated zeolite is then sealed in a mylar foil bag until medical application. Prehydration can also be achieved by mixing a known quantity of water and zeolite in a sealed container. The sealed container can be heated to at least 60° C. and slowly re-cooled to evenly distribute the water amongst the zeolite particles.

Charged Ceramics and Glass Effect

In some embodiments, the invention provides a composition comprising a hemostatically effective amount of a silaceous oxide, ceramic, or nanoceramic. The silaceous oxide, ceramic, or nanoceramic, is selected from the group consisting of: glass beads, silicates, mesoporous silicates, aluminosilicates, aluminophosphates, bioactive glass, titania, alumina, pyrex and quartz. The size and the porosity of the silaceous oxide are selected as appropriate for the desired application. Particle sizes can range from the nanometer to micrometer ranges, with a preference in some embodiments of from 2-15 nm to 10 micrometer, and in some embodiments, for a range of 2-50 nm. Porosity can range from nanoporous to macroporous, with a preference in some embodiments for mesoporous materials. As particle size is decreased, total surface area will increase. The amount of surface area available has been demonstrated as a key parameter in controlling blood clot formation.

In some embodiments, the composition is prepared so as to modulate hemostasis. In some embodiments, the desired modulation comprises an increase in hemostasis, while in others it will comprise a decrease in hemostasis or increased time to coagulation. Such compositions can be used to coat medical devices, such as artificial organs, stents, pumps, sensors and catheters, as well as the interior of containers and passageways that come into contact with blood. When the device has been coated with the composition of the invention, surface induced coagulation is reduced or eliminated.

Antibiotic Activity

In some embodiments, the composition comprises a silaceous oxide in combination with silver or other antibiotic ion. In addition, hemostasis can be accelerated via calcium ion delivery. In some embodiments, the invention provides a material capable of providing for controlled release of a material, such as an antibiotic or other therapeutic agent. The high surface area materials would include nanoparticles, porous particles and porous nanoparticles, particles such as glass beads and $AlPO_4$ (aluminum phosphate) stint-like, particulate, molecular sieve or mesoporous materials, bimodal or polymodal pore structures that have pores of different sizes. Hybrid delivery platforms include those made up of block co-polymer/inorganic composites, or organic-inorganic frameworks such as the organic bridged disiloxane wall structures, and Kuroda-Shimojima's porous silica structure. (Shimojima, A and Kuroda, K. *Angew. Chem. Inl. Ed.* 42, 34, 4057-4060.)

The antibiotic agent scope includes pharmaceutical antibiotics, antibiotic proteins or combinations of therapeutic and antibiotic agents. The porous materials of the invention can have structures with pore sizes that can be varied over a wide range, easily large enough to include antibiotic proteins or other large molecules as well as small molecular therapeutic agents or ionic species and can deliver these agents with controlled programmed release. This can be facilitated by incorporation of molecular units within and attached to pore walls to define the programmed release of the desired agents.

Modification of Oxide Surface

Particle morphology can be selected and designed that enables the delivery or sequestration of electrolytes and water. In addition, the material can be modified by attachment of a biologically active agent, such as recombinant Factor VII, silver ions, heat shock protein (HSP). There are also ways to create high-surface area hemostatic agents. One can increase the internal surface area, which can be measured by BET $N_2$ adsorption. The internal surface area can be controlled by optimizing porosity and/or by use of nanoparticles. For use in the compositions of the invention, one can make porous materials that have surface areas between 1-1000 $m^2/g$, or up to 1500 $m^2/g$. Included in the agents of the invention are nanopores, mesopores, macropores, and micropores (or sub-micropores). Examples of representative pore sizes include 2-50 nm in diameter, 50-100 nm diameter, 100-200 nm, and up to 100-200 μm diameter. Nanoparticles of hemostatic agents that have large surfaces areas can be produced using methods known in the art. One can also increase the biologically available surface area and increase the actual surface of the hemostatic agent that is accessible to larger biological reactants, proteins, cells, etc. For example, one can functionalize the surface of oxides with organosilanes, amino acids, carboxylic acids, and/or phosphate groups, to promote the attachment of clot promoting reactants.

Methods

The invention provides a method of producing a composition for modulating hemostasis, and also a method of modulating hemostasis comprising contacting blood with a composition of the invention. Compositions that modulate hemostasis without generating excessive heat can be prepared by the methods described in the Examples below, including pre-hydration, ion exchange and use of sol-gel chemistry. Sol-gel chemistry can be used to produce bioactive glass. By spraying the sol-gel solution down a hot furnace (e.g., 400° C.), spherical bioactive glass particles are produced. These bioactive glass particles can be as small as 10-50 nm in diameter, or smaller, or as large as about 100 μm or larger. In one embodiment, the particles are 50-200 nm in diameter.

In some embodiments, the method of modulating hemostasis comprises decreasing blood coagulation time. In one embodiment, the time to initiate detectable coagulation (R), as measured by thromboelastograph®, is less than 2 minutes, and can be less than 1.8 minutes. In another embodiment, the rate of coagulation (α), as measured by thromboelastograph®, is more than 50°. Coagulation rates of more than 55°, and of more than 65° have been achieved. In a further embodiment, the coagulation results in a maximum clot strength (MA), as measured by thromboelastograph®, of 55 to 100 mm, and can be less than 75 nm. Alternatively, the modulating comprises increasing blood coagulation time. Increased coagulation time is desirable, for example, when clotting poses a health risk to the subject.

In addition to modulating hemostasis, the compositions of the invention can be used in a method of modulating bone growth. In one embodiment, the method comprises promoting bone growth by contacting bone with a composition of the invention.

Also provided is a medical device and methods of coating a medical device with the composition of the invention. Coatings can be prepared from a composition in powder form or using sol-gel chemistry, using conventional methods known in the art. In one embodiment, the coating reduces coagulation of blood in contact with the device.

EXAMPLES

The following examples are presented to illustrate the present invention and to assist one of ordinary skill in making and using the same. The examples are not intended in any way to otherwise limit the scope of the invention.

Example 1

Formulations of Porous Inorganic Materials for Therapeutic Wound Healing

Figure 1B:
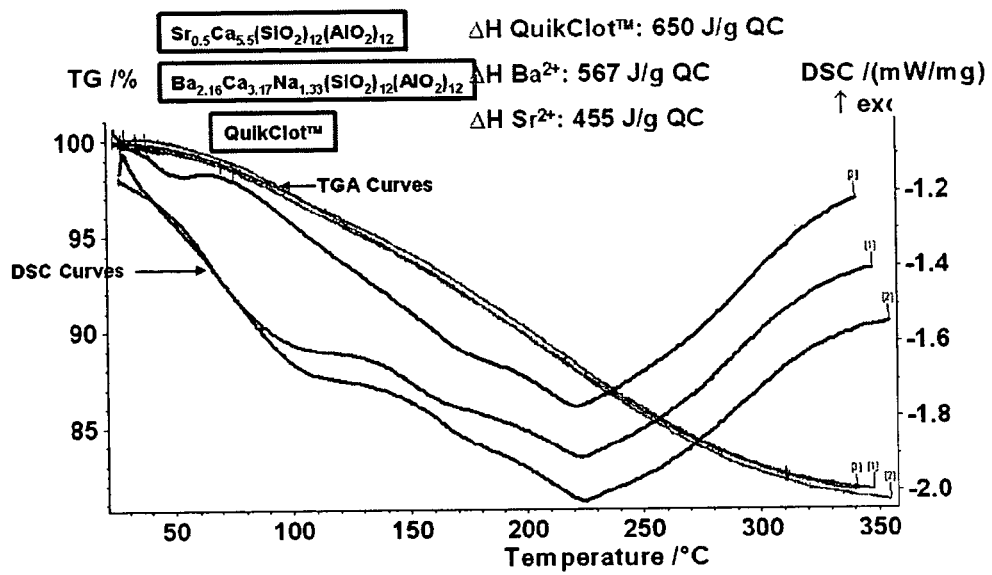
FIG. 1B shows the results of DSC and TGA of QuikClot®, a barium ion exchanged formulation, and a strontium ion exchanged formulation.

This example describes ion exchanged formulations of QuikClot® that reduce the heat of hydration by 5 to 40%. FIGS. 1A-1B show differential scanning calorimetry plots that demonstrate a reduced hydration enthalpy for the ion exchanged formulations. Formulations include mixtures of ion exchanged zeolite Linde Type A with inorganic salts including, but not limited to, calcium chloride ($CaCl_2$) aluminum sulfate ($Al_2(SO_4)_3$) and silver nitrate ($AgNO_3$).

The hydration enthalpy of zeolites is related to the cations present in the zeolite (Yu, BL et al. *Thermochimica Acta*, 200 (1992) 299-308; Drebushchak, V A *J ThermalAnal Calorim-*

*etry* 58 (1999) 653-662; Mizota, T et al. *Thermochimica Acta* 266 (1995) 331-341). Typically, larger and less charged cations tend to have a lower hydration enthalpy. Additionally, the hydration enthalpy of a zeolite relative to the amount of water adsorbed has been found to decrease with increasing water absorption. This means that the primary absorption sites for water in a dehydrated zeolite have the largest associated hydration enthalpies and the final adsorption sites for water have the smallest associated hydration enthalpies.

The application of zeolites as water softening agents is due to their preference for particular cations over other species to charge balance the negative aluminosilicate framework. The zeolite Linde Type A has a known selectivity for cations, and can be prepared with a variety of ionic formulations. These formulations can be designed to exchange ions with a blood solution and act as delivery agents for ions crucial in the blood clotting mechanism. Zeolites can also be prepared to sequester ions from blood, and consequently reduce the clotting activity of the contacted blood. The materials listed herein have been optimized to absorb the necessary amount of water and ion exchange to promote rapid formation of a blood clot in a traumatically injured wound site.

In addition to the ions that can be exchanged directly from the zeolite material itself, small amounts of neutral inorganic salts can also be co-mixed with the zeolite for soluble delivery to the wounded area. In particular, but not limited to these examples, calcium chloride, magnesium chloride, aluminum sulfate, and silver nitrate are co-mixed with the ion exchanged preparations of QuikClot® for delivery of ions that promote therapeutic and antibiotic wound healing. Calcium ions play a ubiquitous role in the blood coagulation cascade (Davie, E W et al. *Biochemistry* 30, 43, (1991) 10363). The additional presence of calcium ions and magnesium ions has been shown to decrease the time to blood clot formation (Sekiya, F et al. *J. Biol. Chem.*, 271, No. 15, 8541-8544). Aluminum sulfate dissolves in aqueous solutions releasing highly charged ionic species. These ions can induce the colloidal precipitation of blood components and further assist in the rapid formation of a blood clot. Silver ions, at low concentrations, have been shown to be effective antibacterial agents. The incorporation of silver nitrate salts with the zeolite A will give added antibacterial activity which will promote a positive wound healing effect.

Figure 2:
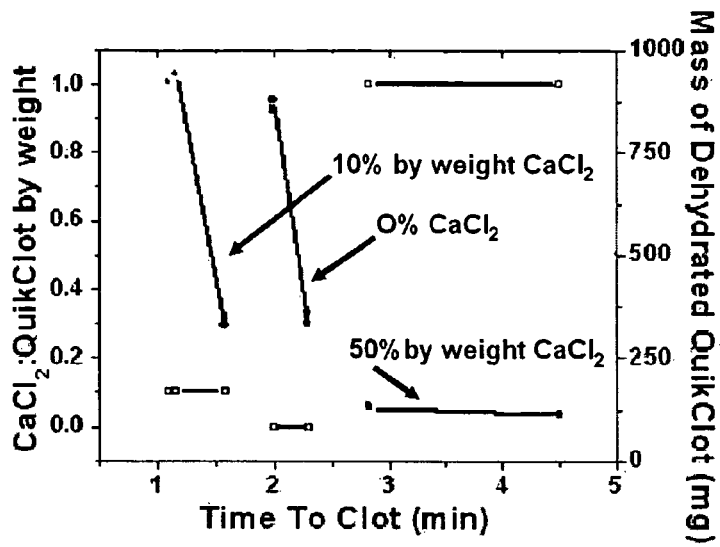
FIG. 2 is a plot of results from a tilt test tube assay of clotting ability of mixtures of calcium chloride and QuikClot®.

The addition of dried calcium chloride to QuikClot® can reduce the time to blood clot formation. This was examined using the tilt test tube assay (and by TEG). FIG. 2 is a plot of the kinetics of blood clot formation. We have further established that the addition of calcium ions during the clotting process significantly increases the blood clot's strength.

Example 2

Hemostatic Effects of Glass and Prehydration: Aantibiotic Activity

This example describes a new class of materials (silaceous oxides and ceramics) which can be co-formulated with QuikClot® or applied directly alone for hemostatic efficacy. In addition, we have substantiated an antibiotic response from QuikClot® towards a typical Gram Negative bacteria.

The Glass Effect

QuikClot® is comprised of a dehydrated zeolite that is applied to the site of traumatic vascular hemorrhaging. At the time of contact with the blood, a large amount of heat is generated at the same time that the zeolite absorbs and sequesters fluid phase components from the blood matrix. It has been observed in our laboratory that, in addition to dehydration and heat generation, there is selective absorption of blood components to the zeolite surface as well as disruption of the local electrolyte concentration. Our initial understanding of the interaction between the four parameters: heat released upon hydration of the hemostatic agent, dehydration capacity of the hemostatic agent, selective surface absorption of blood components, and control of local electrolyte concentrations, has allowed us to identify a class of materials for hemostatic agents that has not been previously identified. These materials are glasses and related oxides that take advantage of the natural interaction between blood and silaceous oxides.

Inorganic oxides inherently carry a surface charge that can be either positive or negative. Zeolites and molecular sieves, as well as many glasses, silicates, and various oxides are significantly charged and will associate with any oppositely charged components of blood when the two come into contact. We present nuclear magnetic resonance (NMR) spectroscopic evidence as well as thromboelastograph(E) plots to substantiate that charged oxides immobilize components of blood and are involved in initiating the blood coagulation event.

Nuclear Magnetic Resonance (NMR) spectroscopy is a technique for identifying molecules based on the energy involved in exciting nuclear transitions when those molecules are subjected to strong magnetic fields. Comparing the $^1$H NMR spectrum of sheep's blood before and after contacting QuikClot® shows that the major changes are occurring in a region normally associated with alkyl protons. After centrifugation, blood will separate into two major fractions. After centrifugation, the plasma phase (top phase) will sit on top of the phase containing the red blood cells and other large solid precipitates. Using this separation technique, we have been able to identify that the majority of the spectral changes are associated with those molecules that reside in the plasma, or top phase after centrifugation. Two major peaks of interest have been observed. A peak at $\delta=2.5$ ppm is apparent whenever the top phase of the blood contacts QuikClot®. The second peak, $\delta=1.7$ ppm, is only observed when the entire blood is not centrifuged, and this intact blood contacts QuikClot®. There is precedent in literature to assign the peak at $\delta=2.5$ ppm to the alkyl region of phospholipids (i.e. sphingomyelin and phosphatidylcholine) that are found in the plasma, or top phase of blood after centrifugation (Murphy, et. al. *Biochemistry* 39 No. 32 (2000) 9763; Yang, et. al. *Anal. Biochemistry* 324, (2004) 29).

A chemical shift anisotropy (CSA) effect is observed for the peak at $\delta=2.5$ ppm. As the sample is spun at a higher rate, the peak at $\delta=2.5$ ppm becomes more symmetric and increases in intensity. This suggests that the molecule associated with this peak is immobilized relative to the surrounding molecules. The $^{31}$p spectrum also suggests that it is a phosphorous containing compound that is becoming immobilized once exposed to the zeolite. Our current understanding of this system involves the selective absorption of at least certain phospholipids from the blood onto the charged oxide.

Figure 3:
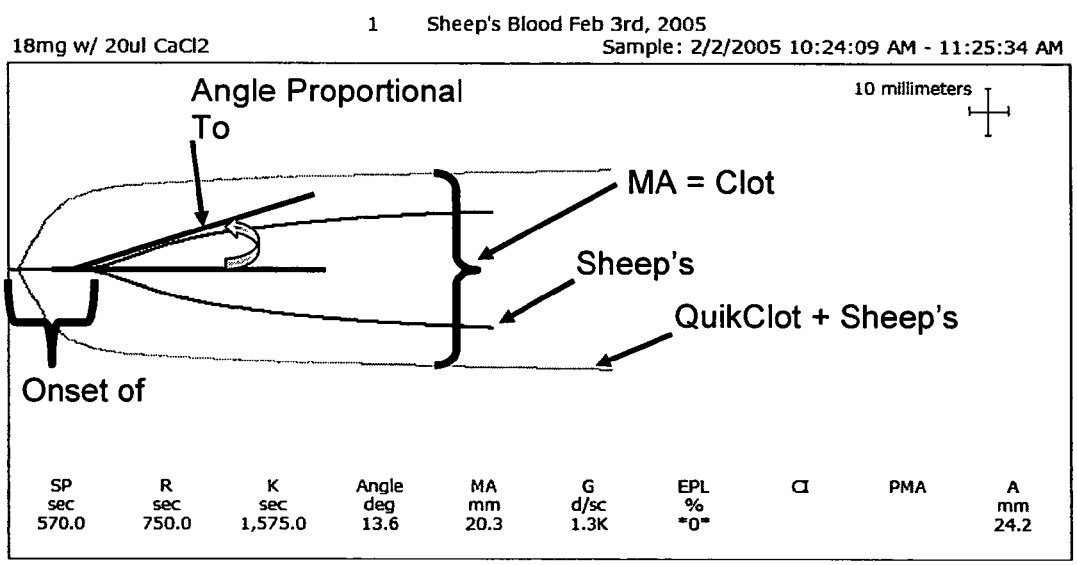
FIG. 3 is a thromboelastograph (TEG) of sheep's blood and sheep's blood with added QuikClot®
Figure 4:
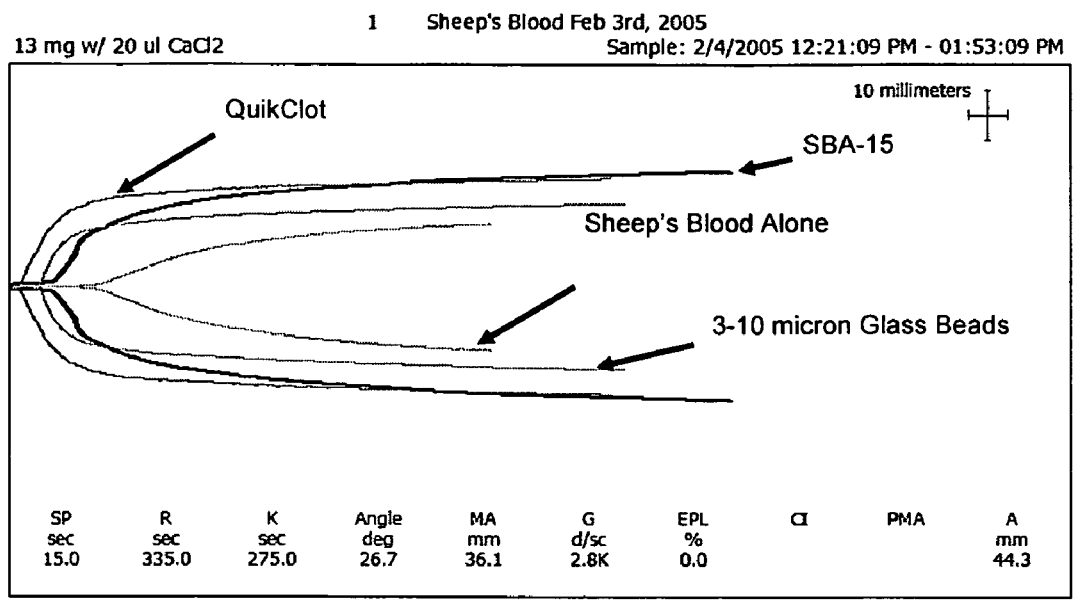
FIG. 4 is a TEG of QuikClot®, SBA-15, and 3-10 micron glass beads.

A thromboelastograph is an instrument that can measure the viscosity change of blood while it is clotting as a function of time. In FIG. 3, a plot is shown of the clotting profile of sheep's blood and sheep's blood exposed to QuikClot®. Various parameters, including the time until the graph splits, the angle the graph rises, and the total separation of the graph are indicative of distinct blood clotting phenomenon. We have been able to demonstrate, as depicted in FIG. 4, that many oxides, including common laboratory glass beads, mesoporous silicates like SBA-15 (Huo, et. al. *Nature* 368, (1994)

317), porous, and non-porous silicates induce blood clotting in a similar fashion to QuikClot®. It is these materials and related silicates, aluminosilicates, aluminophosphates, ceramics, nanoceramics, and oxides, which can be used as hemostatic agents either as co-mixtures with QuikClot® or as hemostatic agents themselves. The advantage of these materials is they have a substantially lower heat of hydration when compared to the original QuikClot® formulation.

Prehydration

The prehydration of QuikClot® can be used to quench the first water absorption sites and thus drastically reduce the total heat of hydration during hemostatic applications. In this example, detailed information related to the amount of heat released as a function of the amount of water absorbed is included to illustrate the optimal hydration formulations for different ionic formulations of QuikClot®.

Figure 5A:
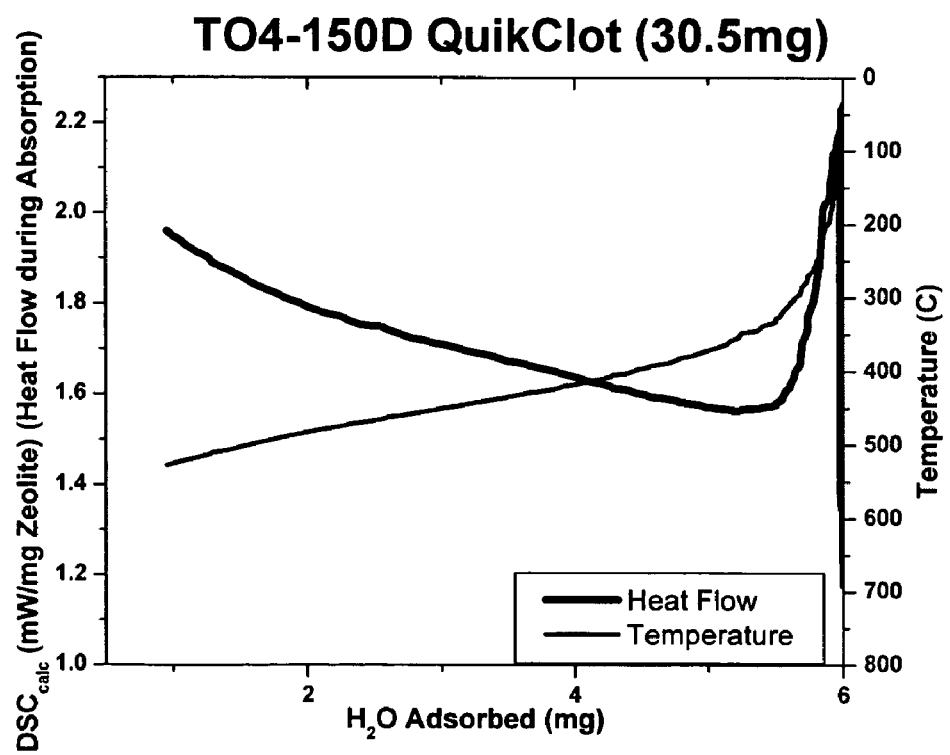
FIG. 5A shows heat of hydration vs. amount of water absorbed for QuikClot®.
Figure 5B:
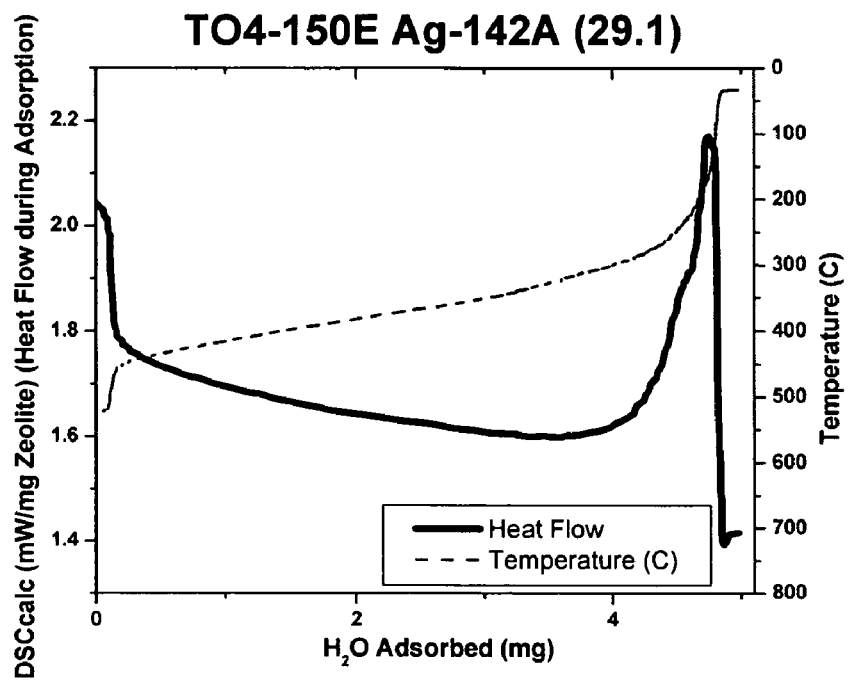
FIG. 5B shows heat of hydration vs. amount of water absorbed for silver loaded QuikClot®.
Figure 5C:
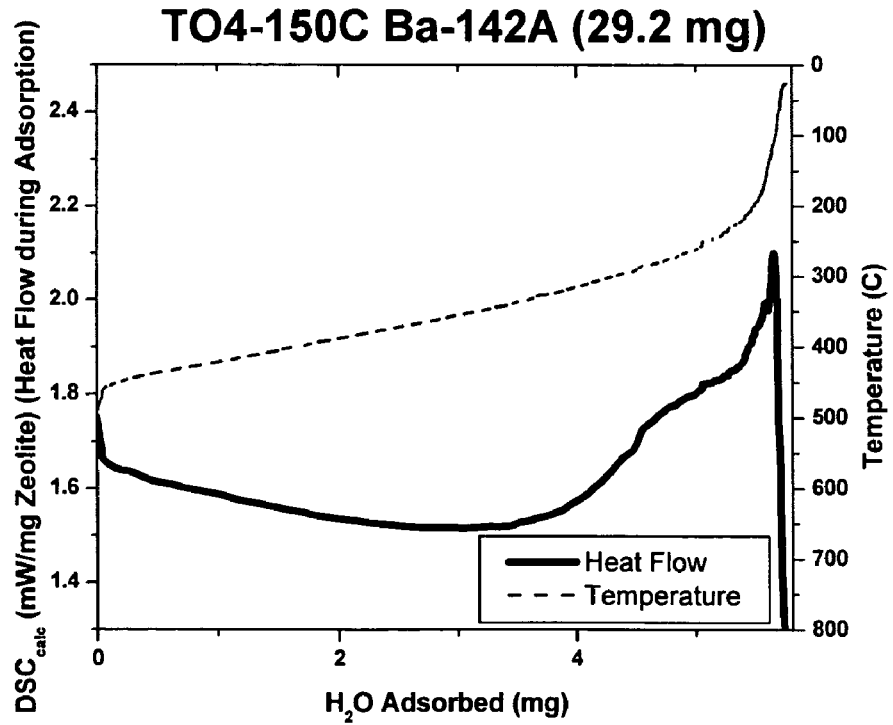
FIG. 5C shows heat of hydration vs. amount of water absorbed for barium loaded QuikClot®.

Differential scanning calorimetry has been used to measure the heat of desorption of water from a hydrated form of QuikClot® as well as hydrated ion exchanged formulations of QuikClot®. Assuming a reversible interaction, it is possible to determine the amount of heat released per amount of water absorbed (Drebushchak, V. A. *J. Thermal Analysis Calonmetry*, 58, (1999), 653). In FIG. 5, the amount of heat released per amount of water absorbed is displayed. It is apparent that the heat of hydration decreases steadily as water is absorbed. Based on this phenomenon, it is ideal to dehydrate QuikClot® to some point below the maximum dehydration capacity. By leaving some residual water behind in the material, the hottest first adsorption sites for water will be quenched. A small amount of prehydration is possible without significantly affecting the hemostatic efficacy of the material.

Antibiotic Activity

A silver loaded formulation of QuikClot® demonstrated antibiotic activity towards Pseudomonas Aeruginosa, a typical Gram Negative bacterium. The silver loaded formulation of QuikClot® released 3 parts per million silver ion concentration into phosphate buffered saline solution. This is well above previously reported antibiotic concentrations and further supports the antibiotic observation with the Gram Negative specie. Silver loaded QuikClot® was added to a few locations on top of the agar in the agar plate. Zones of clearance were quite apparent wherever QuikClot® granules were deposited. These results were confirmed in a further study described in the next example.

Example 3

Host-guest Composites for Induced Hemostasis and Therapeutic Healing in Traumatic Injuries In this example, two strategies for reducing the large amount of heat released by a zeolite-based hemostatic agent (HA) during application have been described and quantified: 1) ion exchange and 2) prehydration. Five ion-exchanged derivatives of the original HA have been prepared and assayed for hemostatic efficacy both in vitro, by TEG®, and in vivo, by clinical swine trials. Contact activation coagulation rates, α, were found to increase with the amount of heat released by the HA. In vitro clot induction time, R, and HA surface area have been identified as predictors of in vivo hemostatic performance. A proposed rationale for selecting hemostatic materials based on these parameters will likely reduce the quantity of experiments involving animals, and the associated labor and capital costs, necessary to test a new HA. A method for incorporating antibacterial activity against gram negative *P. aeruginosa* into the Ag-exchanged formulation of zeolite LTA-5A has been described and substantiated.

In Vitro Thromboelastograph® Analysis

Citrate stabilized sheep blood was obtained from a licensed distributor of animal tissue (Hemostat, Davis, Calif.; Quad Five, Ryegate, Mont.). The study was approved by the Institutional Animal Care and Use Committee at the University of California Santa Barbara in Santa Barbara, Calif.

Clinical Study

Swine survivability rates from a clinical study published elsewhere are solely referenced for discussion purposes and to add relevance to the data included in this report. The Laboratory Animal Review Board for the care and use of animals at the Uniformed Services University of the Health Sciences (USUHS) in Bethesda, MD approved the study. All research was conducted in compliance with the Animal Welfare Act and other Federal statutes and regulations relating to animals and experiments involving animals. The study adhered to the principles stated in the Guide for the Care and Use of Laboratory Animals, National Research Council, 1996 edition.

Materials Preparation

The zeolite Linde type 5A HA was ion exchanged with aqueous solutions of NaCl, KCl, $Ba(NO_3)_2$, $Sr(NO_3)_2$, or $AgNO_3$ depending on which ion was intended for exchange. 300 g of the zeolite Linde type 5A HA was immersed for 2 hours in 1 L of 0.1M aqueous solutions of LiBr, NaCl, KCl, $Ba(NO_3)_2$, $Sr(NO_3)_2$, or $AgNO_3$. Zeolite Linde type 5A was donated by Z-Medica, Inc. The supernatant solution was decanted, and this process was repeated three times with freshly prepared salt solutions. The ion-exchanged products were triple rinsed with IL portions of deionized water to remove unassociated ions. The ion-exchanged products were dehydrated in a shallow bed in a vacuum oven heated to 300° C. at a rate of 5° C./min under $3 \times 10-3$ atm.

The empirical formula for each ion-exchanged HA was determined by X-ray photo-electron spectroscopy (XPS) The empirical formula for each ion-exchanged formulation of zeolite Linde type 5A was calculated by integrating the survey scans collected on a Kratos Axis Ultra XPS spectrometer. All materials studied were stored under vacuum at 60° C. for 12 hours prior to analysis. The ground powders were pressed into tablets attached to double sided copper tape and adhered to the sample holder with the other side of the tape.

Figure 15:
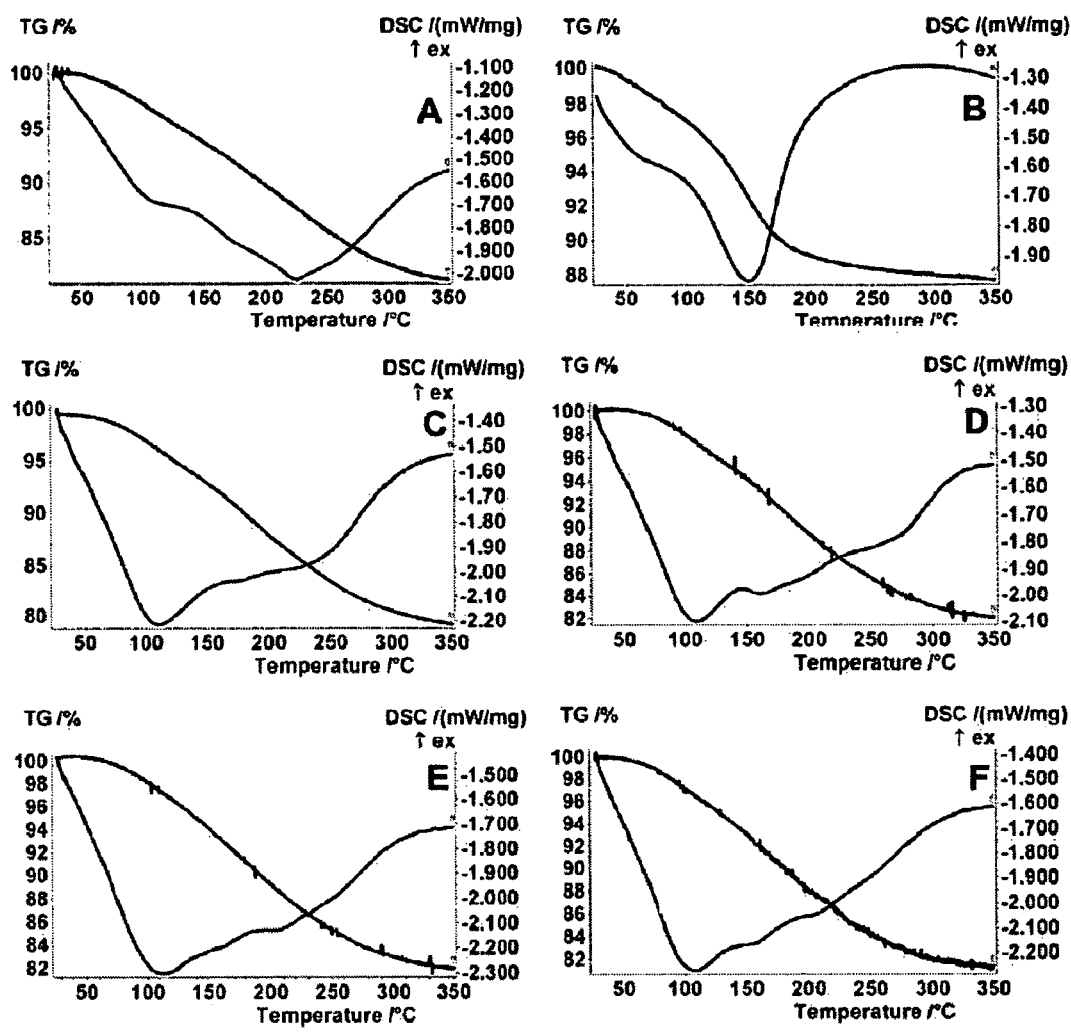
FIG. 15 shows TGA and DSC plots for: A) Zeolite LTA-5A; B) Ag-Exchanged Zeolite LTA-5A; C) Na-Exchanged Zeolite LTA-5A; D) K-Exchanged Zeolite LTA-5A; E) Sr-Exchanged Zeolite LTA-5A; F) Ba-Exchanged Zeolite LTA-5A.
Figure 16:
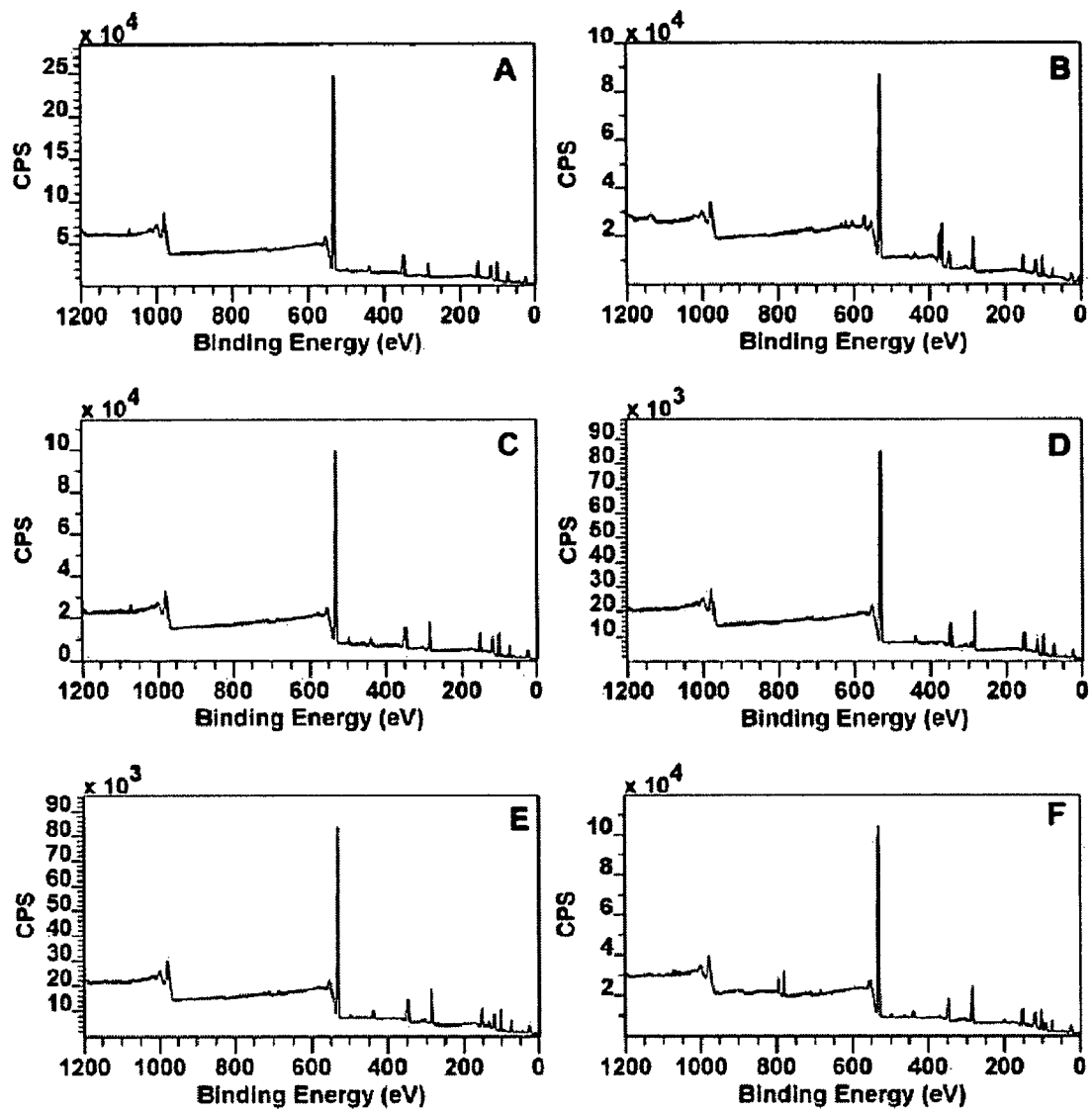
FIG. 16 shows XPS analysis of zeolite based HAs for: A) Zeolite LTA-5A; B) Ag-Exchanged Zeolite LTA-5A; C) Na-Exchanged Zeolite LTA-5A; D) K-Exchanged Zeolite LTA-5A; E) Sr-Exchanged Zeolite LTA-5A; F) Ba-Exchanged Zeolite LTA-5A.
Figure 17A:
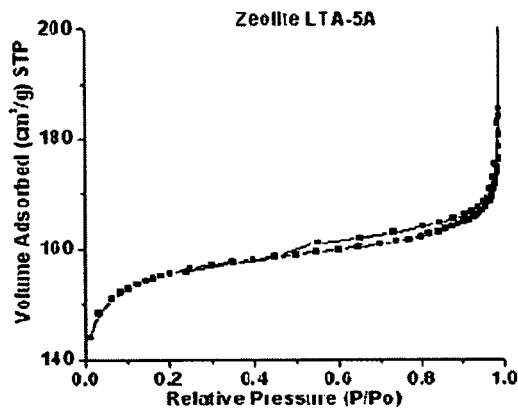
FIGS. 17A-F show BET $N_2$ adsorption isotherms of HAs.
Figure 17B:
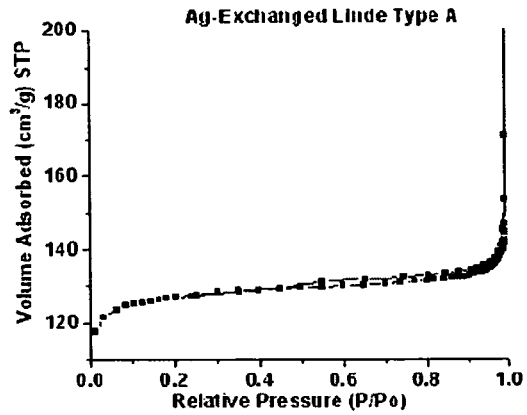
Figure 17C:
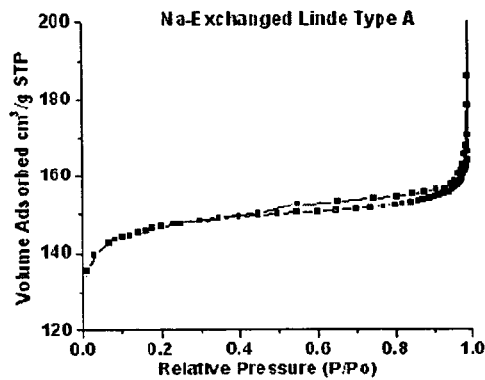
Figure 17D:
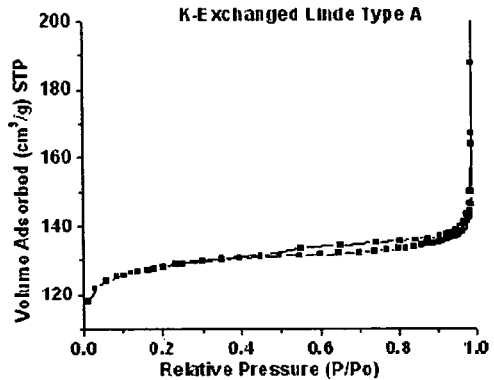
Figure 17E:
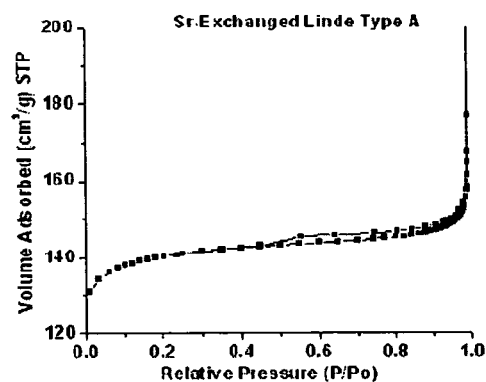
Figure 17F:
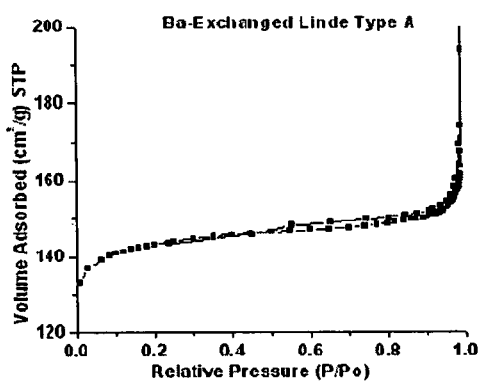

FIG. 15 contains thermogravimetric and differential scanning calorimetry plots for all HAs analyzed. Crystal phase identification was determined by X-ray powder diffraction (XRD). X-ray powder diffraction patterns were collected on a Scintag X2 instrument using monochromatic Cu Kα radiation. Samples were ground in a mortar and pestle prior to diffraction analysis. FIG. 16 contains X-ray photoelectron spectroscopy plots of each HA from which the empirical formulas were calculated. Surface areas were measured by BET $N_2$ adsorption. Surface area analysis of each material was performed using a Micromeritics TriStar 3000. 80-150 mg of each zeolite based HA was placed in BET sample tubes and dehydrated under flowing $N_2$ at 200° C. for 12 hours. Surface area was calculated using the BET model. FIGS. 17A-17F contains BET surface area analysis for the HAs.

Scanning Electron Microscopy (SEM)

SEM images were obtained using an FEI XL40 Sirion FEG Microscope. Samples were deposited on Al stages and sputtered with a Au/Pt alloy. Images were collected with an accelerating voltage in the range of 2-5 kV.

Zeolite particles were dipped into a small pool of freshly extracted human blood, obtained by a minor needle pierce to a finger tip. Prior to imaging, the particles were washed with phosphate buffered saline solution to remove material not fully adhered.

Thermal Gravimetric Analysis (TGA) and Differential Scanning Calorimetry (DSC)

The standard protocol for determining the heat of hydration for zeolites is to measure the heat of desorption of water from a hydrated zeolite and then assume a reversible hydration reaction (Drebushchak, V. A. *J. Thermal Analysis Calorimetry*, 58 (1999) 653). Ion exchanged zeolite HAs were stored for two weeks in enclosures suspended over a Petri dish containing a saturated water solution of KBr, which maintains 80% relative humidity.

A Netzch STA 409C was employed to quantify the heat associated with the desorption of water from the zeolite. 10-15 mg of each hydrated zeolite was placed in an aluminum crucible with a loosely attached aluminum lid; an empty aluminum crucible and lid was used as the reference cell. Each sample was heated from 20° C. to 350° C. at a rate of 10° C./min. The hydration capacity of each HA was measured by thermogravimetric analysis (TGA) of water loss, and simultaneously collected differential scanning calorimetric (DSC) curves were integrated to obtain the total heat for the dehydration reaction. (See FIG. 15.)

Thermal Iimaging

A direct measure of the in vitro increase in temperature of the HAs with application was determined by thermal imaging using a Santa Barbara Focal Plane liquid nitrogen cooled ImagIR LC camera. The thermal imaging camera was calibrated for the temperature range between 20° C. and 100° C. This methodology can be used for in vivo applications as well. Experiments were filmed at 28 Hz frame rate. A Janos Technology A ISO 25 mm F/2.3 MWIR focusing lens was attached to the camera.

TEG® Analysis of Induced Clot Formation

A thromboelastograph®, Haemoscope model 5000, was used to acquire in vitro clotting parameters for sodium citrate (4% v/v) stabilized sheep blood exposed to the tested hemostatic materials (Blood obtained from Quad Five, Ryegate, Mont.). Prior to the addition of a HA, 20 µL of 0.2 M aqueous $CaCl_2$ was added to 340 µL of the stabilized sheep blood to replenish the citrate chelated $Ca^{2+}$ ions and restore the blood's clotting activity. HAs were dehydrated and stored in an argon atmosphere prior to analysis.

20 mg of a zeolite-based HA was introduced directly into the TEG® sample cup containing the sheep blood and re-supplied $Ca^{2+}$ ions. The sample cup was rotated ±5° about a torsion wire suspended in the middle of the rotating sample. As the hardening blood clot tugs on the torsion wire, the change in viscoelastic clot strength (sheer elasticity) is monitored as a function of time (see FIG. 10). The time until the curve of clot strength splits is referred to as the R time, and represents the initial detection of clot formation. The angle between the tangent to the rising curve and the horizontal is referred to as the α parameter. The α parameter is related to the rate of coagulation. The maximum separation of the viscosity curve split is referred to as the MA parameter and represents the maximum clot strength. A list of the TEG® parameters obtained for the tested HAs is tabulated below (see Table 3).

Antibacterial Assay

*Pseudomonas aeruginosa* PG201 (Urs Oschner, University of Colorado) was cultivated overnight at 30° C. on Luria-Bertani (LB) agar from archived (−80° C.) stock culture. After inspecting for purity, a single colony was dispersed into 2 mL of sterile 0.9% NaCl in Nanopure water. Spread (LB agar) plates were prepared from 100 µL of the suspension. Bactericidal activity of the tested material was assessed by depositing granules and pressed pellets of the HAs onto spread plates and incubating the plates for 24 hours at 30° C. The relative bactericidal activity was evaluated by measuring the zone of no growth (zone of clearing) around the pellet (see Table 4). The vertical and horizontal dimensions of the zones of no growth around 1 cm pellets was measured for five identical samples and averaged.

In vivo Sswine Assay Model

The in vivo performance of the ion exchanged HAs was assayed at the Uniformed Services University of the Health Sciences in Bethesda, Maryland. A report detailing the clinical application of the modified HAs to a lethal swine groin injury will be published as Ahuja, et. al., *J Traum*, 2006. The swine survivability rates from these trials were discussed at a recent military medical research conference (Alam Hasan B. Zeolite Hemostatic Dressing: Battlefield Use. In: Advanced Technology Applications for Combat Casualty Care (ATACCC); 2005 August 15-17; St. Petersburg, Fla.; 2005). These survivability rates are included herein to add relevance to the in vitro TEG® analysis and materials characterization. The in vitro TEG® method for testing inorganic HAs was developed prior to the clinical swine trials and involved the use of sheep blood, arguably the most widely used specie for in vitro hemodynamic studies. By identifying the critical in vitro TEG® clotting metrics and materials properties that correlate with in vivo swine survivability, it should be possible to better predict the performance of the next generation of HAs without relying extensively on animal trials for each new formulation.

The procedure for testing the in vivo performance of zeolite-based HAs has been previously described (Alam HB, Kheirabadi BS, *J Trauma* 2005;59(1):34-35; Alam HB et al. *J Trauma* 2003;54(6):1077-1082). Briefly, a lethal groin injury is induced in an anesthetized Yorkshire swine (40-55 kg) by transection of the proximal thigh soft tissues (skin, quadriceps, adductor muscles), and complete division of the femoral artery and vein just below the inguinal ligament. After 3 minutes of bleeding, the ion exchanged HAs are poured directly into the hemorrhaging wound and external pressure is applied by the physician. The physicians conducting the trials have no knowledge of which HA they are testing until after the study is complete.

Composition and Morphology of the Zeolite Based HA

Figure 6:
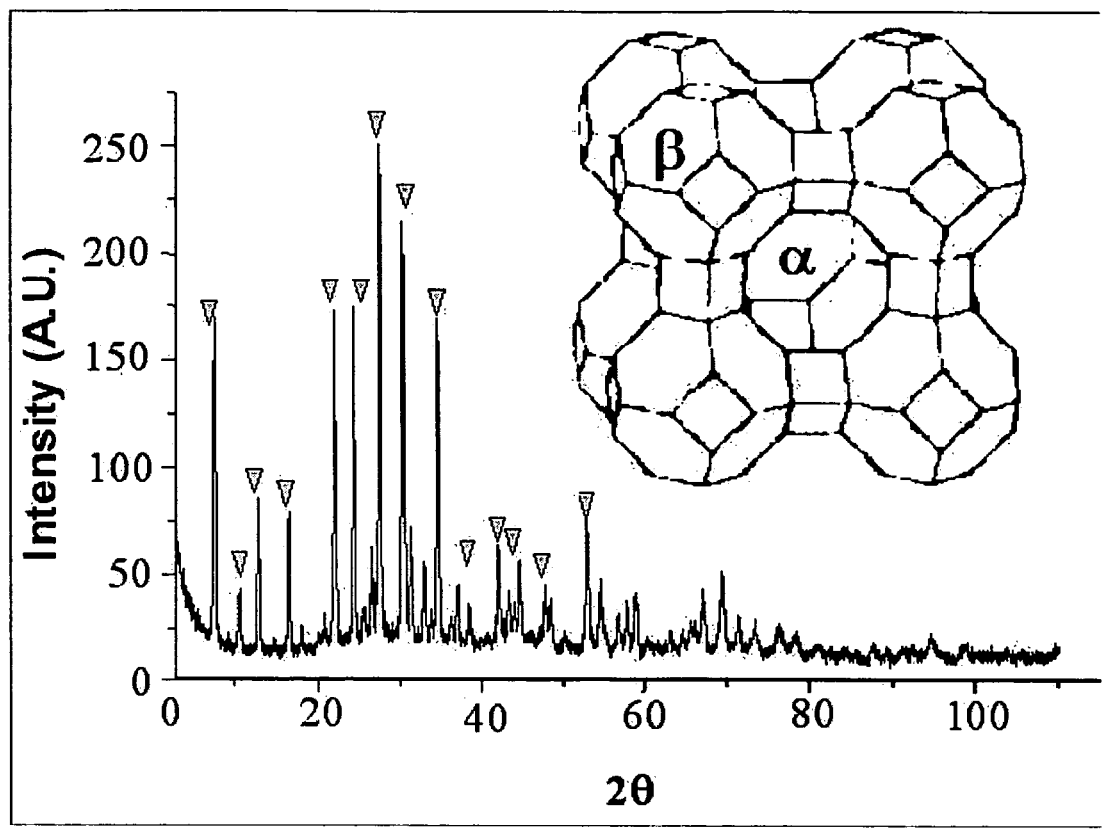
FIG. 6 is a powder X-ray diffraction pattern of QuikClot®. The triangles identify reflections associated with the zeolite LTA-5A. Inset is a schematic of the zeolite LTA structure where each vertex represents alternating Si and Al atoms and the straight lines represent bridging oxygen atoms. The α-cage is 11.4 Å in diameter and the β-cage is 6.6 Å in diameter. The α-cage pore aperture is ~4 Å in diameter.
Figure 7A:
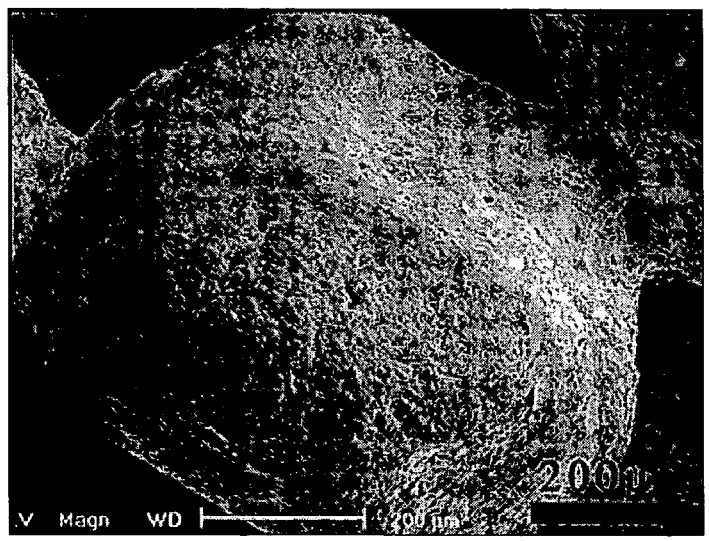
FIG. 7A is a scanning electron micrograph showing zeolite LTA-5A granules.
Figure 7B:
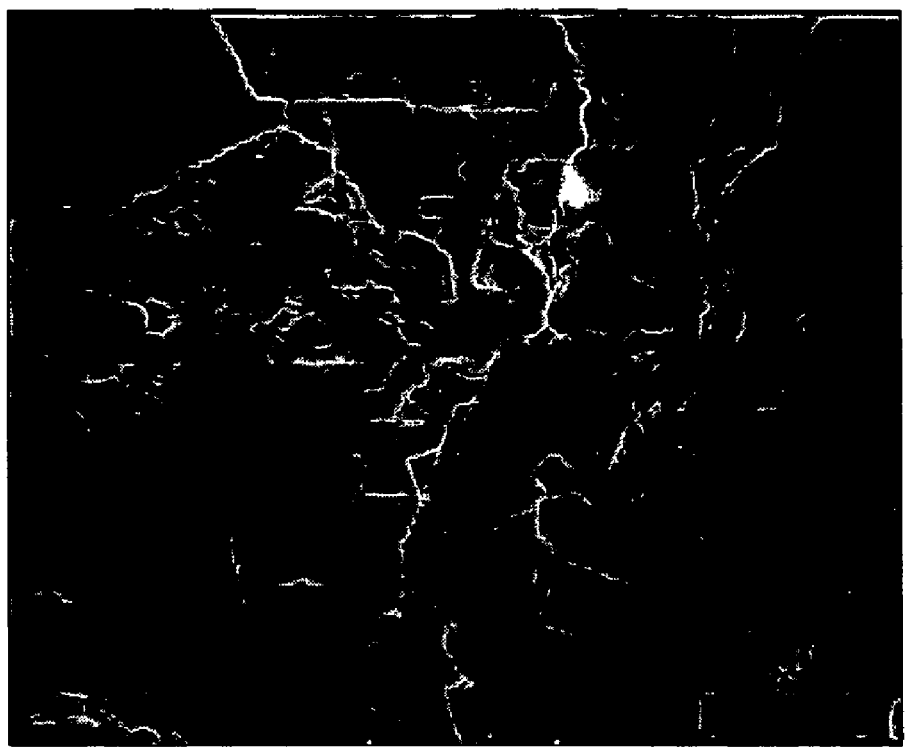
FIG. 7B is a scanning electron micrograph showing ground zeolite LTA-5A.
Figure 7C:
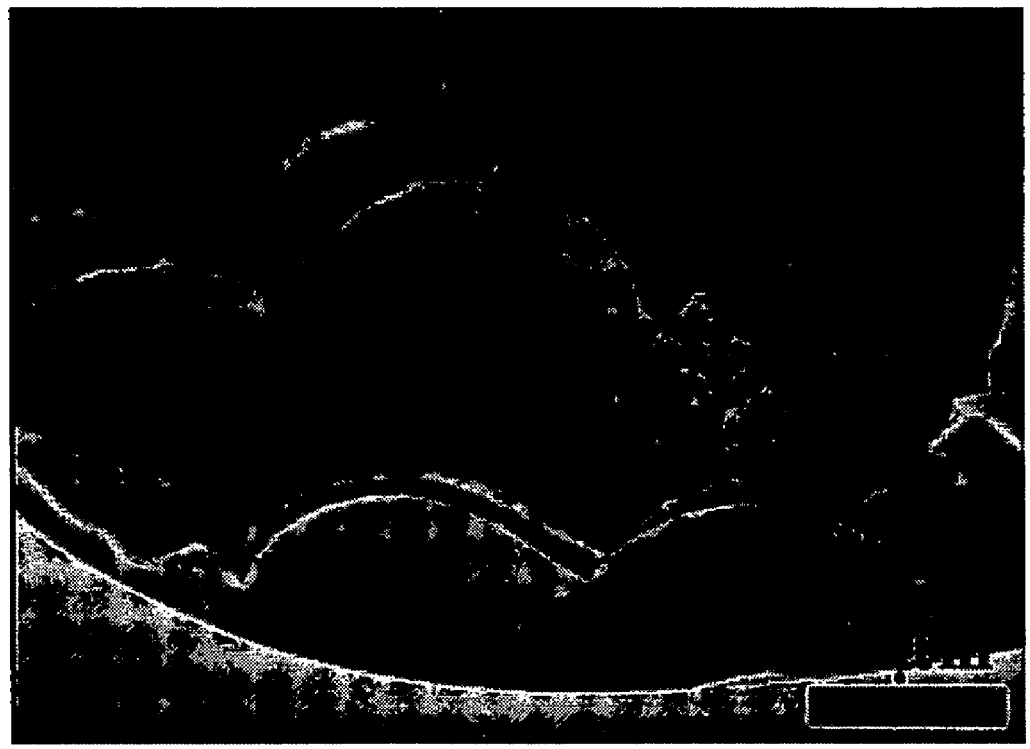
FIGS. 7C and 7D are a scanning electron micrographs showing human blood cells adhered to zeolite LTA-5A crystals.
Figure 7D:
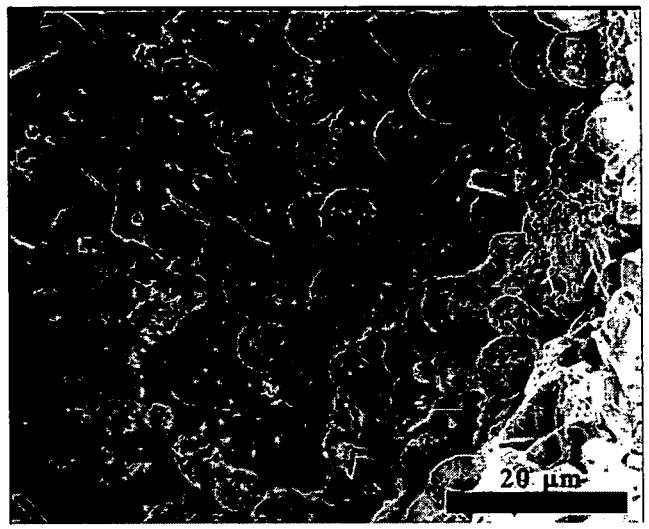

The X-ray diffraction pattern of QuikClot® (FIG. 6) confirms that the major active constituent is the zeolite Linde type 5A, commonly referred to as Calcium-A. The ratio of Si:Al is equal to 1, and the empirical formula of the material is determined by XRD, TGA, and XPS to be $Na_{0.5}Ca_{5.75}(SiO_2)_{12}(AlO_2)_{12} \cdot 27H_2O$ when fully hydrated (FIG. 6, 8, 16). There are two interior porous cages where the positively charged $Ca^{2+}$ and $Na^+$ cations reside. The larger is called the α-cage and is 11.4 Å in diameter. The smaller is called the β-cage and is 6.6 Å in diameter. The pore apertures, of the α-cage, through which adsorbable molecules enter, are 4 Å in diameter. The significance of this aperture dimension is that the most probable constituents of blood that are able to enter the zeolite's porous crystal bulk are small entities such as water and electrolytes (e.g. $Na^+$, $Ca^{2+}$). The zeolite affinity for water is high, and thus application of the zeolite to blood has a concentrating effect on the plasma by selectively dehydrating the blood. A consequence of this affinity for water is a significant release of energy upon hydration.

QuikClot® is packaged as granules ~600 μm in diameter. These granules are composed of a crystalline component and an amorphous binder. Scanning electron micrographs of the zeolite LTA-5A before and after contacting blood (FIG. 7) demonstrate that blood cells adhere to the HA and are dehydrated, causing a change in cellular morphology. It is also worth noting that the zeolite crystallites have dimensions on the order of blood cells, 1-2 μm and 5 μm respectively.

Heat of Hydration

The primary goal of this research was to identify strategies to reduce the excessive amount of heat generated by the HA during application without adversely affecting the wound healing properties. Two methods for attenuating the HA's heat of hydration, 1) ion exchange and 2) prehydration, are analyzed by TGA and DSC. TGA is used to measure the mass loss of water from a saturated zeolite as a function of temperature, and DSC is used to quantify the heat associated with this process. The reversible heat of hydration for each HA was calculated by integrating the DSC response.

Figure 8:
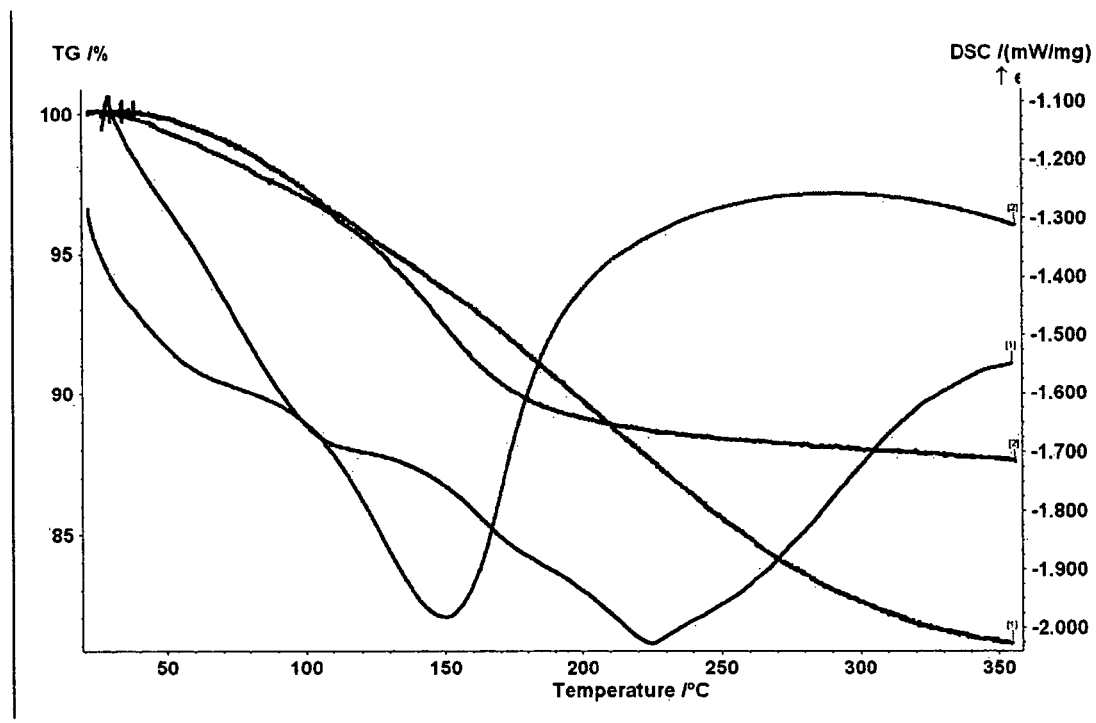
FIG. 8 shows TGA and DSC responses for zeolite LTA-5A and Ag-Exchanged zeolite LTA-5A.

The original HA can absorb close to 20% water by weight and releases 680 Joules of energy per gram of zeolite upon hydration. After ion exchanging the $Ca^{2+}$ and $Na^+$ ions in the original HA with $Ag^+$ ions ($Ag_{3.26}Ca_{4.30}(SiO_2)_{12}(AlO_2)_{12} \cdot xH_2O$), the silver-load absorbs 12% water by weight and releases 420 J/g of zeolite. The shift of the DSC curve minima to lower temperatures when the original HA is ion exchanged with $Ag^+$ ions is indicative of the reduced energy of attraction between the adsorbed water molecules and $Ag^+$ ions in the modified zeolite compared to the $Ca^{2+}$ ions that are present in the original HA formulation. (FIG. 8)

In addition to the $Ag^+$-ion-exchanged formulation, a series of alkali metal and alkaline earth metal ion exchanged formulations were prepared. The empirical formula, hydration capacity, and heat of hydration for each formulation are listed below (Table 1, See FIG. 15 for TGA and DSC plots of each ion exchanged HA.). Analogous to Coulomb's law ($E_{Attraction} \alpha (Q_1 * Q_2)/r$ where Q is the magnitude of charge and r is the distance of interaction), the energy of attraction between a polar water molecule and monovalent ions tends to be lower than for divalent ions of the same size, and also tends to be lower for larger cations compared to smaller ions of the same valency. Despite zeolite LTA-5A's 5 varying selectivity for each ion which limits the ion-loading capacity, the substitution of a portion of the $Ca^{2+}$ ions in the original HA with $Na^+$, $K^+$, $Sr^{2+}$, $Ba^{2+}$, or $Ag^+$ ions results in a reduced heat of hydration.

TABLE 1

Hydration capacity (% w) and heat of hydration (J/g) for a series of ion exchanged formulations of zeolite LTA

| Molecular Formula | Hydration capacity (% by weight) | Surface Area ($m^2/g$) | $\Delta H_{Hydration}$ (J/g zeolite) |
|---|---|---|---|
| QuikClot ™ $Na_{0.5}Ca_{5.75}(SiO_2)_{12}(AlO_2)_{12} \cdot xH_2O$ | 20 | 632 | 680 |
| Na-Exchanged Linde Type A $Na_{0.6}Ca_{5.7}(SiO_2)_{12}(AlO_2)_{12} \cdot xH_2O$ | 21 | 457 | 640 |
| K-Exchanged Linde Type A $K_{1.12}Ca_{5.44}(SiO_2)_{12}(AlO_2)_{12} \cdot xH_2O$ | 18 | 363 | 584 |
| Sr-Exchanged Linde Type A $Sr_{0.63}Ca_{5.37}(SiO_2)_{12}(AlO_2)_{12} \cdot xH_2O$ | 18 | 281 | 650 |
| Ba-Exchanged Linde Type A $BaCa_5(SiO_2)_{12}(AlO_2)_{12} \cdot xH_2O$ | 19 | 634 | 600 |
| Ag-Exchanged Linde Type A $Ag_{3.36}Ca_{4.30}(SiO_2)_{12}(AlO_2)_{12} \cdot xH_2O$ | 12 | 723 | 420 |

A second strategy, in addition to ion exchange, to reduce the heat of hydration of the original HA is to prehydrate the HA before medical use. The heat generated during hydration of a zeolite is largest at the beginning of rehydration, when the initial adsorption sites become saturated, and continually decreases as more water is adsorbed. Thus the "hottest" adsorption sites for the HA are the first sites for water condensation. By prehydrating the original zeolite LTA-5A 1% by weight, it is possible to reduce the total heat generated by ~⅔ (Table 2). By prehydrating the Ag-exchanged HA by 1%, the total heat generated can be reduced by ½. Although this heat reduction strategy has been identified and quantified, the clotting properties of prehydrated zeolites are not discussed in this report. The prehydration strategy serves only to highlight alternative methods of achieving the same reduced heat of hydration.

TABLE 2

Total heat (J/g) generated (calc.) during application of HA if prehydrated

| Sample | $\Delta H_{Hydration}$ 0% Prehydration | $\Delta H_{Hydration}$ 1% Prehydration | $\Delta H_{Hydration}$ 3% Prehydration |
|---|---|---|---|
| Zeolite LTA-5A | 680 J/g | 415 J/g | 253 J/g |
| Ag-Exchanged zeolite LTA-5A | 420 J/g | 212 J/g | 111 J/g |

Thermal Imaging

DSC is necessary to quantify the heat released upon hydration of a dehydrated zeolite (i.e. Q), but this measurement alone is insufficient to predict the actual temperature the HA will heat to when applied to a hemorrhaging wound. The change in temperature of matter associated with heat flow is $\Delta T = Q/(m*C_p)$; where $\Delta T$ is the change in temperature, Q is the amount of heat, m is the mass of matter, and $C_p$ is the heat capacity of the matter. Thermal imaging can dynamically monitor the in vitro rise in temperature which will be a function of the amount of water absorbed, the rate of absorption, and the wound geometry.

Figure 9:
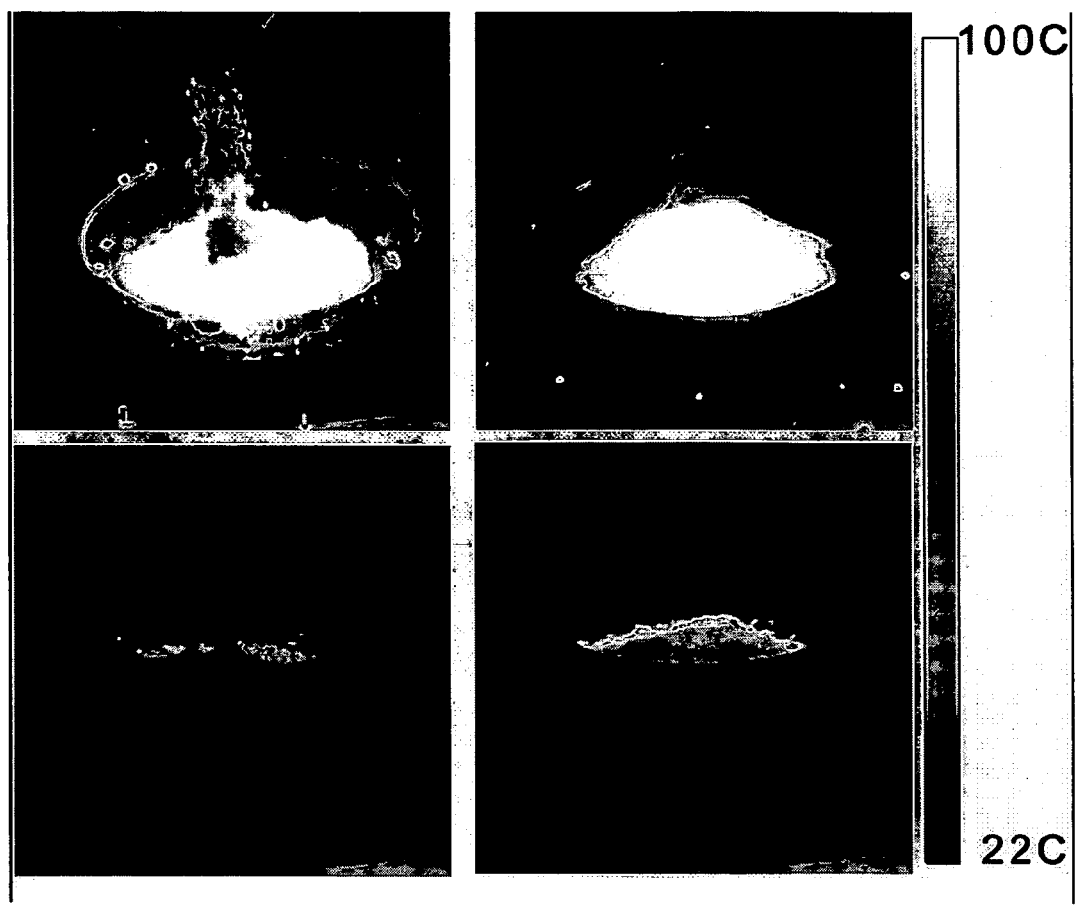
FIG. 9 shows maximum temperature measured in vitro with the thermal imaging camera for the hydration of zeolite LTA-5A (Top) and Ag-exchanged zeolite LTA-5A (Bottom). From left to right: Zeolite is poured from the top of the frame into a Petri dish of water. Initial image is on left, final image is on right. Color Gradient: White represents 100° C. and black represents 22° C. Field of view is approximately 12 cm×12 cm.

Thermal imaging is a non-invasive method for acquiring a 3-dimensional illustration of the heat propagation and final temperature of the hydrated HA without introducing foreign objects that would affect the heat response. This technique allows for precise measurements of temperature for small scale experiments where the heat capacity of the materials and the quick temperature change render using a thermometer impractical. Each video was recorded as 5 g of a zeolite HA was poured into a dish containing 5 ml of water. Selected frames from the thermal imaging videos acquired while pouring the dehydrated zeolites into a container of water demonstrate the range of temperatures that can be achieved (FIG. 9). This approach could also be directly applied for in vivo monitoring of the thermal effects of thrombosis and thrombolysis. The zeolite affinity for water is so great that the HA material is observed to be heating from atmospheric water absorption while falling through the air and before contacting the dish of water below. After fully hydrating, the original HA formulation heated to 95° C. while the Ag-exchanged formulation heated to 38° C. The Ag-exchanged HA did not heat much above human body temperature (37° C.), however, the original HA would likely cause severe burning to biological tissue if applied in a similar fashion.

TEG® Analysis of Induced Thrombosis

Figure 10:
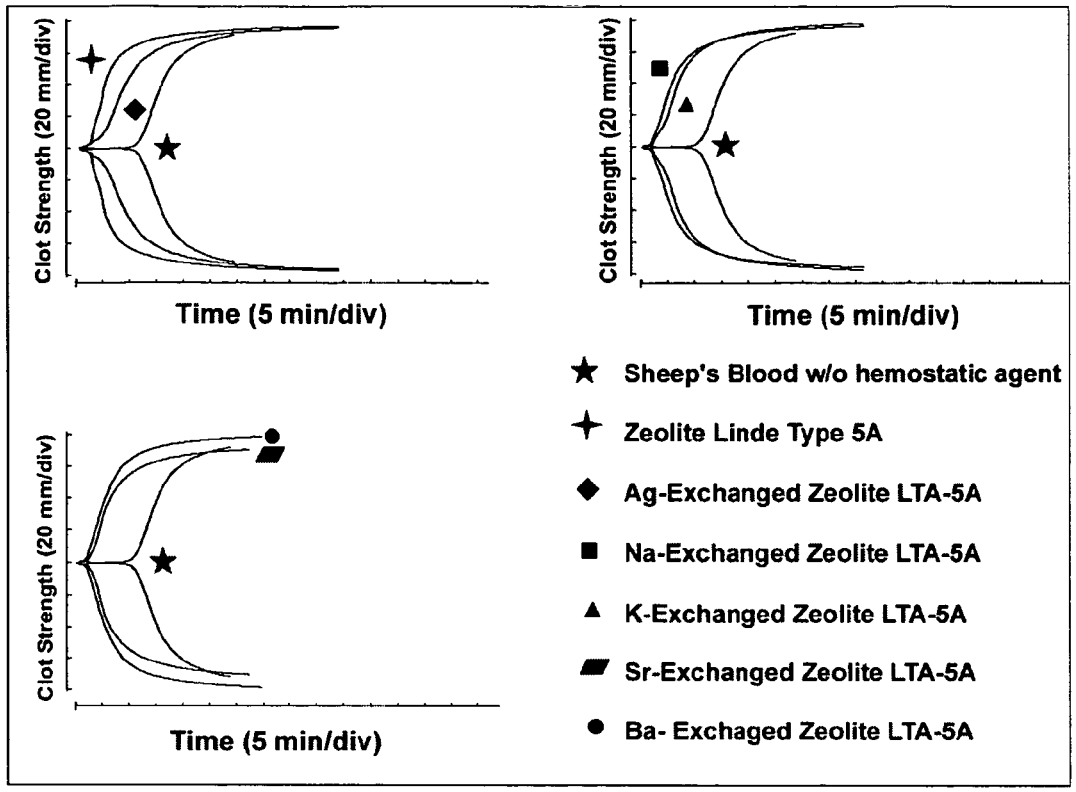
FIG. 10 shows thromboelastograph® plots. Top-left: Silver exchanged formulation of zeolite LTA-5A. Top-right: alkali-metal ion exchanged formulations of zeolite LTA-5A. Bottom: alkaline earth metal ion exchanged formulations of zeolite LTA-5A.
Figure 11:
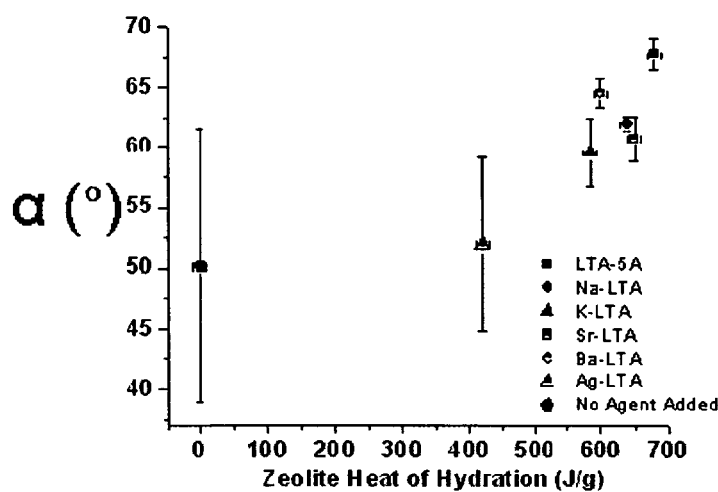
FIG. 11 is a plot of in vitro coagulation rate parameter, α (°) as a function of the heat of hydration (J/g) released by a zeolite HA. Vertical bars represent±one standard deviation of the data.
Figure 14:
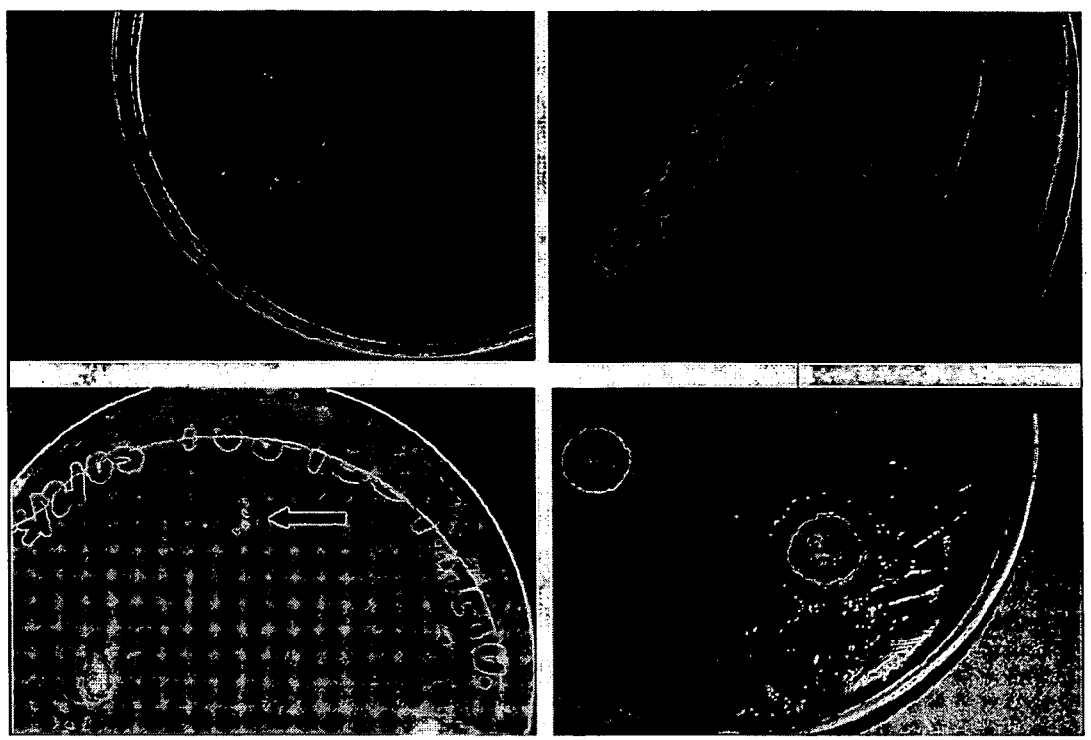
FIG. 14 shows optical pictures of *P. aeruginosa* bacterial biofilms. Top-left: Cross streaked LB-agar plate of bacteria grown for purity assay and single colony collection. Top-right: Zeolite LTA-5A granules with bacterial biofilm overgrown on top of zeolite particles. Bottom-left: Zones of clearance of the bacterial film in the vicinity of the Ag-exchanged zeolite LTA-5A formulations. Bottom-right: Zones of clearing of the bacterial biofilm in the vicinity of pressed pellets of powdered Ag-exchanged zeolite LTA-5A formulations. (White streaks in top right and bottom left frames are reflections from room lights.)

TEG® is a standard method for surveying the induced thrombotic effects of hemostatic materials and quantifying the onset of coagulation, R time (min), the rate of coagulation, α (°), and the maximum clot strength (MA)(mm). A 0.2 M $CaCl_{2(aq)}$ solution was added to the sheep blood immediately prior to the addition of the zeolite HAs to replenish the $Ca^{2+}$ ions chelated by the citrate stabilizing molecule. The TEG® profiles and tabulated clotting parameters for the zeolite-based HAs are listed below (FIG. 10, Table 3). Without adding any inorganic agent, sheep blood begins to clot with an average R=10.9 min and with an alpha parameter of 50.2°. All of the zeolite HAs initiated coagulation in less time, R≦2.2 min, and with an accelerated rate of coagulation, α≧52°, compared to sheep blood alone. There is a clear relationship between the heat released by the HA and the rate of induced coagulation (FIG. 11). There was no noticeable effect on ultimate clot strength, MA, with the addition of the HAs.

as evidenced by the zones of clearance of the bacterial biofilm around the Ag-exchanged zeolite particles (FIG. 14). An average zone of no growth diameter of 1.45 cm was observed after 24 hours of incubation (Table 4). Relative to the 1 cm HA pressed pellet, the geometrical surface area of the zone of no growth was greater than that of the pellet by a factor of ~2.2. The zone of clearance for the Ag-loaded material was preserved over time suggesting that the minute amount of released silver ions are indeed bactericidal and do not simply slow down the bacterial growth. Except for the Ag-exchanged formulation, the original HA and all the other ion-exchanged formulations, were neither bactericidal nor bacteristatic against *P. aeruginosa*, and bacterial biofilm growth was observed both under and on the pellets.

TABLE 3

In vitro TEG ® clotting parameters. Mean values and standard deviation listed. Swine survivability percentages for ion exchanged zeolite LTA-5A also listed.

| HA | R (min) σ | α (°) σ | MA (mm) σ | Swine Survivability (%) |
|---|---|---|---|---|
| Ag-Exchanged Linde Type A | 0.9 | 52.0 | 75.6 | 75 |
| | 0.7 | 7.2 | 8 | 6 out of 8 survived |
| Ba-Exchanged Linde Type A | 1.8 | 64.6 | 76.9 | 75 |
| | 0.2 | 1.2 | 1.2 | 6 out of 8 survived |
| Na-Exchanged Linde Type A | 21 | 62.0 | 73.3 | 57 |
| | 0.2 | 0.6 | 1.2 | 4 out of 7 survived |
| K-Exchanged Linde Type A | 2.2 | 59.6 | 77.5 | 0 |
| | 0.6 | 2.9 | 0.9 | 0 out of 2 survived |
| Sr-Exchanged Linde Type A | 2.1 | 60.8 | 73.7 | 0 |
| | 0.2 | 1.9 | 2.6 | 0 out of 2 survived |
| Citrated Sheep Blood + $CaCl_{2(aq)}$ | 10.9 | 50.2 | 77.4 | n/a |
| | 1.3 | 11.3 | 2.5 | |
| Zeolite Linde Type 5A | 1.8 | 67.8 | 79.6 | ~100 |
| | 0.1 | 1.3 | 1.1 | * Reference 2a |

Predicting In Vivo Survivability by Identifying Critical In Vitro Parameters

The in vivo survivability of the ion exchanged formulations was assayed. In these experiments, a universally lethal battlefield injury was simulated by completely severing the femoral artery and vein of a swine at the level of the inguinal ligament. The zeolite based HAs were then applied after 3 minutes of bleeding to control the hemorrhage in the injured animal. The Ag-exchanged and the Ba-exchanged formulations of the zeolite LTA-5A were observed to result in the highest survivability, with 75% (6 out of 8) of the animals surviving. The Na-exchanged formulation resulted in more than half of the swine surviving the traumatic injury, 57% (4 out of 7). The Sr-exchanged and the K-exchanged formulations resulted in the lowest survival rates with all of the swine perishing following the femoral artery injury (0 out of 2 survived).

Figure 12:
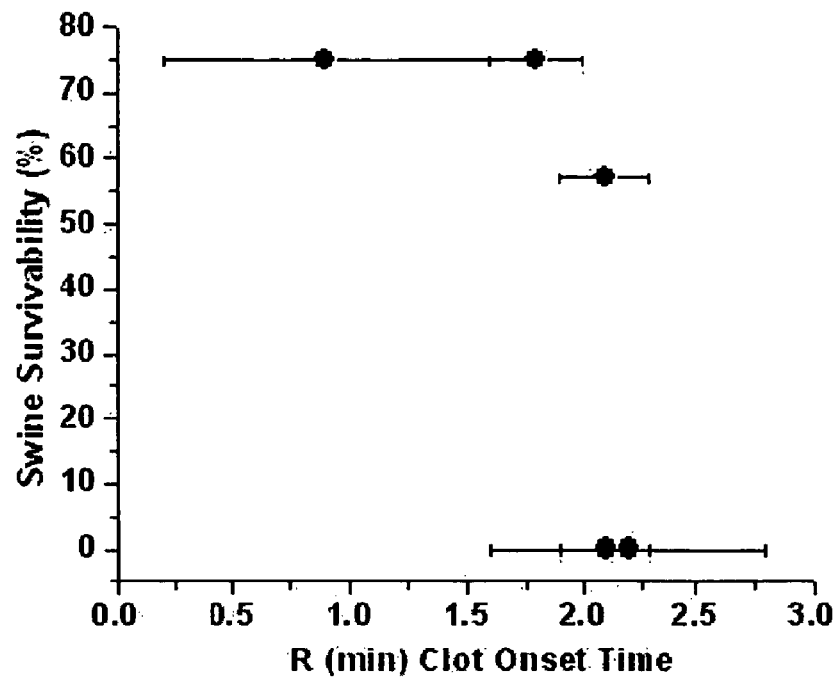
FIG. 12 is a plot of swine survivability versus average clot induction time, R (min). Horizontal bars represent±one standard deviation of the data.
Figure 13:
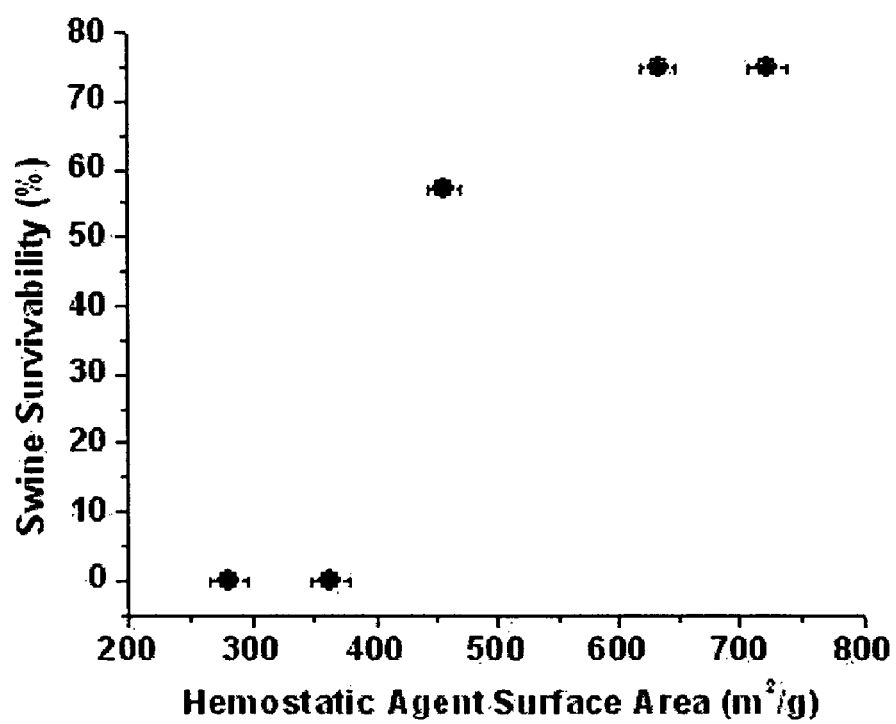
FIG. 13 is a plot of swine survivability versus surface area ($m^2/g$) of HAs. Horizontal bars represent±one standard deviation of the data.

Although all of the ion-exchanged HAs tested in vivo demonstrated accelerated in vitro clotting profiles relative to sheep blood alone, only those agents with an average in vitro clot induction time of R≦1.8 correlate with 75% swine survivability (FIG. 12). There was also a positive trend with regard to the surface area of the HAs and swine survivability. Those agents with a surface area ≧634 m²/g correlate with 75% swine survivability (FIG. 13).

Antibacterial Activity

Antibacterial activity of zeolite LTA-5A and the ion-exchanged formulations was tested against a common opportunistic Gram Negative pathogen, *P. aeruginosa*. Only the Ag-exchanged formulation exhibited clear antibacterial activity

TABLE 4

Zone of no growth of *P. Aeruginosa* around pressed pellets of HAs.

| Hemostatic Agent 1 cm diameter pressed pellets | Antibacterial (yes/no) | Zone of No Growth Diameter (cm) after 24 hours | Zone of No Growth Surface Area:Pellet Geometric Surface Area |
|---|---|---|---|
| Ag-exchanged LTA-5A | Yes | 1.45 ± 0.06 | ~2.2 |
| Zeolite LTA-5A | No | 0 | 0 |

Induced Coagulation by Zeolite Hemostatic Agents

Zeolite-based HAs are a light-weight high-surface-area material that can be applied to a variety of traumatic injuries to control hemorrhage and stabilize victims until more sophisticated care giving facilities are available. The accelerated coagulation response induced by zeolite-based HAs is due to multiple factors including plasma metabolite concentration, contact activation of the blood clotting cascade, and thermal warming of the injured tissue. Zeolites can sequester a large amount of water (20% by weight) and this will concentrate plasma metabolites in the hemorrhaging blood. The polar aluminosilicate framework of the zeolite is an ideal surface for the activation of the intrinsic pathway of the blood clotting cascade. Hematological researchers are familiar with the phenomena, referred to as the "glass effect", where blood tends to clot faster on polar glass-like surfaces than on less polar plastic-like surfaces. The current understanding is that polar surfaces are involved in the autocatalytic activation of clotting Factors XII and XI along with prekallikrein and cofactor HWK-kininogen and $Ca^{2+}$ ions. Zeolite based HAs are a novel example of a medical device designed to treat traumatic injuries in part due to their ability for accelerated contact activation. Because zeolites have minimal bio-incorporation during medical application, are designed to deliver and sequester bioactive ions, and can be tuned with regard to thermal warming and local dehydration of biological tissue, they are an ideal material platform for designing HAs.

Although the excessive heat released by the original HA tends to burn healthy tissue, there is a relationship between the rate of thrombosis and the heat released by the zeolite HA (FIG. 11). Recent studies also suggest that the coagulation rate is related to temperature, as well as concentration, and local electrolyte conditions (Wolberg AS et al. *J Trauma* 2004;56(6):1221-1228). Heating the wound to some extent should accelerate clot formation, however, heating to the point of burning tissue is not necessary. Because the "host-guest" nature of zeolites allows for fine tuning of their chemical, physical and thermal properties (Helfferich F. Ion Exchange. New York: McGraw-Hill Book Company, Inc.; 1962), these materials can be formulated for a variety of wound healing scenarios.

Tunable Thermal Response

The host-guest nature of zeolite-based materials allows for a tunable response with regard to thermal application and hydration capacity. This report focuses on two strategies for reducing the heat released by the original zeolite HA, ion-exchange and prehydration. By selecting an appropriate cation to ion-exchange with the parent material, it is possible to achieve temperatures between 38° C. and 100° C. for the hydration of a fully dehydrated zeolite (FIG. 9). The interaction between $Ag^+$ ions and water is less favorable than between $Ca^{2+}$ ions as evidenced by the migration of the DSC curve mima to lower temperatures for the Ag-exchanged HA compared to the original formulation. Further reduction of the heat of hydration is possible with additional ion exchange, however, the formulations included in this report are those that resulted in the fastest in vitro initiation of blood coagulation. Certain ion exchanged formulations of zeolite LTA-5A, not included in this work, could sequester calcium ions from a wound, and this was detrimental to rapid clot formation regardless of how minimal the associated heat of hydration.

Because the heat generated during hydration decreases as a function of the amount of water absorbed, it is possible to further reduce the total heat generated by careful prehydration of the HA. For example, our results show that by quenching the primary adsorption sites with $^1$% prehydration of the Ag-exchanged zeolite the total heat generated is reduced by ½ (Table 2). By prehydrating the sample, temperatures close to human body temperature are easily achieved.

In Vitro Clot Induction Time, R, HA Surface Area and In Vivo Hemostatic Efficacy Before testing a HA on human subjects, it is necessary to follow rigorous animal testing protocols to insure that human patients do not unnecessarily suffer in the pursuit of medical discovery. Animal testing can be extremely expensive, not to mention time consuming for the medical professionals who care for the animals before, during, and after experimentation. The materials that were sent for clinical testing at USUHS were selected based on their ability to have a reduced thermal response upon hydration but also an accelerated in vitro coagulation response relative to sheep blood alone. All of the reduced-hydration-enthalpy formulations that were analyzed in the swine assays fit these criteria, but their in vivo performance was not indicative by the in vitro results alone. By identifying the most critical in vitro clotting parameters that can predict in vivo hemostatic efficacy, it will be possible to better select the next generation of HAs for clinical trials. This will likely reduce the overall need for animal experiments to develop improved HA materials.

In order to stabilize a patient with a life threatening hemorrhage, it is important to initiate the formation of a blood clot as soon as possible. There is a clear relationship between the onset time of clot formation measured by TEG® and the survivability of swine. Average in vitro clot induction times of R=1.8 min or less are associated with at least 75% of swine surviving a breach of the femoral artery (FIG. 12). Average R parameters greater than 2.1 minutes are associated with a significant number of swine subjects perishing. Short onset time measured by TEG should be a paramount consideration for any newly designed HA prior to the involvement of animal testing.

Recent work has introduced the importance of available surface area for clotting reactions to proceed (Hoffman M. *J Thromb Thrombolys* 2003;16(1-2):17-20). Essential complexes of proteins, carbohydrates, phospholipids, and ions, including the "tenase" complex and thrombin enzyme, require heterogeneous catalytic surfaces (i.e. platelet cellular surface) to become activated for thrombosis. There exists a positive correlation between the surface area of the zeolite HAs and the swine survivability (FIG. 13). The HAs with the highest swine survivability, Ag-exchanged LTA-5A and Ba-exchanged LTA-5A, also have the largest surface area, 723 $m^2/g$ and 634 $m^2/g$ respectively. HAs with surface areas less than 457 $m^2/g$ resulted in a significant number of swine perishing. Because the pore apertures of zeolites are small (~4 Å), the only surface area available for cellular and large biological molecules to interact with is the peripheral surface of the granular particles. The extensive surface area within the internal porous architecture will affect rates of hydration, hydration capacity, and ionic mobility. It is therefore reasonable to conclude that HAs with large internal surface areas are desirable for rapid acting clotting agents.

Antibacterial Activity

Silver ions in parts per billion concentrations are known to have antibacterial properties against both gram positive and gram negative bacteria. A fortunate consequence of ion-exchanging LTA zeolites with silver ions is a reduction in the heat of hydration while simultaneously affording antibiotic activity. The Ag-exchanged formulations demonstrated this activity against *P. aeruginosa* in the LB agar assays. A zone of no growth about twice the dimensions of the HA was preserved over a twenty four hour period. This type of antibacterial technology should find widespread application due to the ease of incorporation into medical materials.

Zeolite-based HAs have demonstrated high survivability for remediating life threatening hemorrhages in real world scenarios despite the potential for tissue damage due to the exothermic heat of hydration side effect. Two strategies, 1) ion exchange and 2) prehydration, have been identified for reducing the heat released during application of the HA. Five distinct ionic formulations of the parent HA have been prepared and their material, thermal, and in vitro clotting characteristics described. In vitro blood clotting parameters have been correlated with in vivo hemostatic performance to identify the most critical parameters that predict hemostatic efficacy. This report includes the first TEG® analysis of induced blood clot formation by inorganic materials. Clot induction time, R, and surface area of the HA are critical parameters affecting hemostatic efficacy. There is also a positive relationship between the rate of contact activated coagulation and the amount of heat released by the HA. These trends should improve methods for selecting the next generation of HAs, and thus reduce unnecessary animal involving experiments and the associated labor and capital costs. A method for incorporating antibacterial activity into hemostatic materials has also been described and substantiated for the Ag-exchanged formulation of zeolite LTA-5A against gram negative *P. aeruginosa*.

Example 4

Oxide Hemostatic Activity

In this example, the tunable in vitro hemostatic activity of high-surface-area bioactive glass (BG) is evaluated by Thromboelastograph®, a standard medical instrument for quantifying viscoelasticity changes of blood during thrombosis and fibrinolysis. The hemostatic trends associated with BG, and a new preparation of spherical BG, along with similar Si and Ca containing oxides, are described and related to Si:Ca ratios, $Ca^{2+}$ availability and coordination environment, porosity, $\Delta H_{Hydration}$, and surface area. This report represents a novel hemostatic application for a material already well respected as a wound healing agent.

Contact activation of blood, commonly referred to as the "glass effect", is the process by which polar surfaces activate the intrinsic pathway of the blood clotting cascade and the underlying principle for the observation that blood tends to clot faster on glass surfaces than on plastic. The autocatalytic activation of clotting Factors XII, XI, prekallikrein, and high-molecular-weight kininogen is initiated by exposure of blood to a foreign polar surface, and this in turn activates the numerous feedback mechanisms responsible for the association of the thrombin enzyme and the polymerization of fibrin. Essential to these chemical dynamics are surface area for immobilizing participants of surface-dependent clotting reactions and $Ca^{2+}$ ions, which are co-factors that help to orientate protein assemblies and enzymes responsible for fibrin production (e.g. tenase complex).

Developed by Hench and coworkers in the late 1970's for bone repair, BG is a composite material of the general formula SiO2—CaO—P$_2$O$_5$—MO (M=Na, Mg, etc.) (Hench, L. L., *J. Am. Ceram. Soc.* 1998, 81, 1705). We identified BG as an ideal inorganic HA because BG will release $Ca^{2+}$ ions upon hydration, and is comprised of an insoluble core that could provide an effective support for thrombosis. We have prepared a new high-surface-area porous BG that demonstrates accelerated in vitro apatite growth when immersed in simulated body fluid. We have extended this sol-gel synthetic preparation to include spray pyrolysis at 400° C. in a tube furnace to prepare the new spherical BG.

Synthesis of Bioactive Glass Hemostatic Agents

Porous bioactive glass hemostatic agents were prepared by a sol-gel evaporation induced self-assembly process that used tetraethyl orthosilicate, Ca(NO3)2, and triethyl phosphate as inorganic precursors and a triblock copolymer poly(ethyleneoxide)-poly(propylene oxide)-poly(ethylene oxide) (Pluronic P123, EO20PO70EO20) as a structure directing agent. The synthesis of non-porous bioactive glass consists of the same synthesis without incorporating P123. An ethanol solution of P123 20% w/w was first prepared. A separate solution of 15% water, 5% HCl, 40% inorganic precursors, and 40% w/w ethanol was prepared. The mole fraction of P relative to Si and Ca was kept at 4% for all bioactive glass materials.

The precursor sol was mixed with the copolymer solution in a ratio of 1:1 in a Petri dish and dried at 60° C. for 8 h to cross-link the inorganic precursors. For non-porous bioactive glass, pure ethanol is used in place of the 20% w/w ethanol solution of P123. The product was calcined in air at 550° C. for 4h to remove the block copolymer.

Spherical bioactive glass was prepared by spraying the sol-gel solution described above down a horizontal tube furnace heated to 400° C. The calcined spherical bioactive glass was collected on filter paper in a collection trap set up at the terminal end of the horizontal tube furnace. A schematic of the spray pyrolysis setup is shown below.

X-ray Photoelectron Spectroscopy

A Kratos Axis Ultra x-ray photoelectron spectrometer was used to determine the empirical formula, ratio of Si:Ca, and Ca 2p electron binding energies in the oxide HAs. All materials were stored under vacuum at 60° C. for 12 hours prior to analysis.

The ground powders were pressed into tablets attached to double sided copper tape and adhered to the sample holder. Spectra referenced to the C 1s peak at 285 eV.

Thromboelastograph® Analysis of Blood Clot Formation

A thromboelastograph®, Haemoscope Model 5000, was used to assay the in vitro hemostatic activity of the BG HAs by introducing 20 mg of a dehydrated HA (heated to 100° C. under vacuum and stored in an argon glove box) into the polyethylene sample cup containing 340 µL of 4% v/v citrate-stabilized sheep blood (Blood purchased from Quad Five of Ryegate, Mont.) with 20 µL of 0.2 M CaCl2(aq). 20 µL of 0.2 M aqueous CaCl2 was added to the stabilized blood to replenish the Ca2+ ions chelated by citrate, which was added to prevent coagulation of stored blood. Blood stored at 8° C.

The thromboelastograph® sample cup is rotated ±5° about a vertical torsion wire suspended in the middle of the cup. As the hardening blood clot tugs on the torsion wire, the change in viscoelastic clot strength (viscoelasticity) is monitored as a function of time.

TABLE 5

Thromboelastograph ® Clotting Properties for BG HAs.

| Bioactive Glass | Si:Ca | R (min) | α (°) | MA (dyn/cm2) |
| --- | --- | --- | --- | --- |
| Sheep Blood | 0 | 10.9 | 50.2 | 58 |
| BG60NP | 0.26298 | 4 | 58.2 | 80.6 |
| BG60 | 0.37622 | 4.1 | 69.4 | 69.8 |
| BG65NP | 0.39035 | 5.2 | 63.8 | 76.9 |
| BG70NP | 0.39639 | 5.9 | 58.8 | 68.5 |
| BG75NP | 0.80638 | 4.5 | 70.9 | 74 |
| BG80NP | 1.2071 | 3.8 | 71.7 | 74.8 |
| BG60SPNP | 1.45929 | 3 | 75.3 | 69.8 |
| BG60SP | 1.60423 | 4.5 | 71.7 | 69.5 |
| BG80 | 1.75583 | 3.6 | 71.1 | 78.2 |
| BG65 | 2.43451 | 4.1 | 70.6 | 63.4 |
| BG80SPNP | 2.46971 | 2.7 | 76.1 | 72.7 |
| BG70 | 2.48523 | 3.4 | 77.9 | 75.2 |
| BG75 | 3.65146 | 4.1 | 73.2 | 77 |
| BG90NP | 4.00235 | 3.8 | 72.3 | 74.4 |
| BG 90 | 5.25349 | 4.3 | 70.1 | 78.7 |
| BG80SP | 5.94941 | 2.9 | 79.8 | 69.4 |

TABLE 6

Thromboelastograph® Clotting Properties for Oxide HAs.

| Hemostatic Agent | R (time) | α (°) | MA (dyn/cm2) |
|---|---|---|---|
| CaO | 5 mg: 2.2 | 34.5 | 91.8 |
|  | 10 mg: 2.8 | 47.8 | 93.1 |
|  | 15 mg: 1.7 | 53.9 | 92.8 |
| CaCO₃ | 5 mg: 10.9 | 33.6 | 61.3 |
|  | 10 mg: 9.2 | 38 | 64 |
|  | 15 mg: 7.1 | 47.4 | 70.3 |
| SBA-15 | 5 mg: 5.9 | 56.2 | 65.7 |
|  | 10 mg: 5.2 | 49.9 | 66.2 |
|  | 20 mg: 4.7 | 32.6 | 67.9 |
| Glass Beads | 5 mg: 4.4 | 60.6 | 65.7 |
|  | 10 mg: 3.7 | 65.4 | 66.2 |
|  | 20 mg: 3 | 71.5 | 67.9 |
| Hydroxylapatite | 5 mg: 13.8 | 41.5 | 63.9 |
|  | 10 mg: 13.6 | 38.4 | 60.5 |
|  | 15 mg: 20.5 | 11.3 | 35.5 |
|  | 20 mg: 22.8 | 7.3 | 29.45 |

Thermal Gravimetric Analysis (TGA) and Differential Scanning Calorimetry (DSC)

The standard protocol for determining the heat of hydration for porous oxides is to measure the heat of desorption of water from a hydrated oxide and then assume a reversible hydration reaction. HAs were stored for two weeks in enclosures suspended over a Petri dish containing a saturated water solution of KBr, which maintains 80% relative humidity. A Netzche STA 409C was employed to quantify the heat associated with the desorption of water from the HAs. 10-15 mg of each hydrated HA was placed in an aluminum crucible with a loosely attached aluminum lid; an empty aluminum crucible and lid was used as the reference cell. Each sample was heated from 20° C. to 350° C. at a rate of 10° C./min. The hydration capacity of each HA was measured by thermogravimetric analysis (TGA) of water loss, and simultaneously collected differential scanning calorimetric (DSC) curves were integrated to obtain the total heat for the dehydration reaction.

TABLE 7

Hydration capacity and $\Delta H_{Hydration}$ (calc.) for selected HAs.

| Hemostatic Agent | Hydration Capacity (% w/w) | $\Delta H_{Hydration}$ (calc.) (J/g) |
|---|---|---|
| Porous BG60 | 14 | 463 |
| Porous BG80 | 20 | 451 |
| Non-porous BG60 | 2.5 | 72 |
| Non-porous BG80 | 2.5 | 82 |
| SBA-15 | 8 | 350 |
| QuikClot® | 20 | 700 |

BET Surface Area Analysis

BET nitrogen adsorption-desorption isotherms and pore size distribution measurements were performed on a Micromeritics Tristar 3000. Samples were dehydrated under flowing $N_2$ at 200° C. for 12 hours prior to BET analysis.

TEM Sample Preparation

Spherical BG was ground and dispersed in isopropanol. One droplet of this cloudy solution was deposited on a lacy carbon TEM grid. Samples were imaged on a FEI Technai G2 Sphera at 200 kV accelerating voltage.

TABLE 8

BET surface area analysis of BG

| Hemostatic Agent | Surface Area (m2/g) |
|---|---|
| Porous BG60 | 339 |
| Porous BG80 | 420 |
| Porous spherical BG80 | 386 |
| Non-porous BG60 | 123 |
| Non-porous BG80 | 197 |
| SBA-15 | 1000 |
| QuikClot® | 600 |

Figure 18:
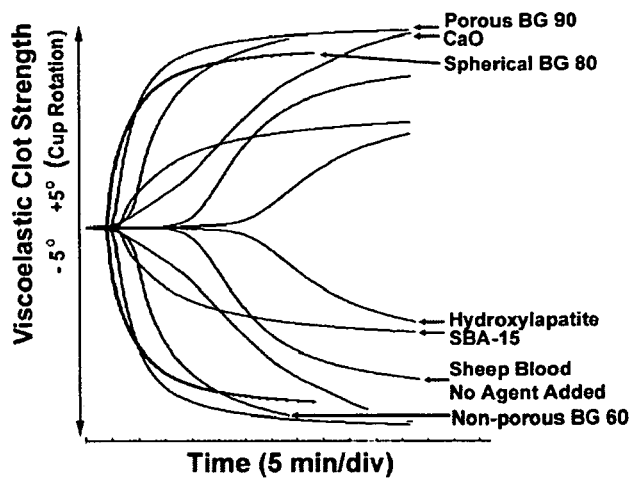
FIG. 18 shows oxide thromboelastograph® plots.

Thromboelastograph® is an instrument used to diagnosis blood disorders by monitoring the change in viscoelasticity of blood during clot formation as a function of time (Haemoscope Corporation, Niles, Ill.). A polyethylene cup, containing blood and a HA, is rotated ±5° about a torsion wire. The time until the bimodally-symmetric viscoelasticity curve's amplitude is 2 mm is referred to as R (min), and represents the initial detection of clot formation. The angle between the tangent to the curve and the horizontal is referred to as α(°), and is related to the rate of coagulation. The maximum separation of the curves is referred to as MA and represents the maximum clot strength (dyn/cm²). An overlay of representative Thromboelastograph® plots for the materials studied is shown below (FIG. 18).

Figure 19:
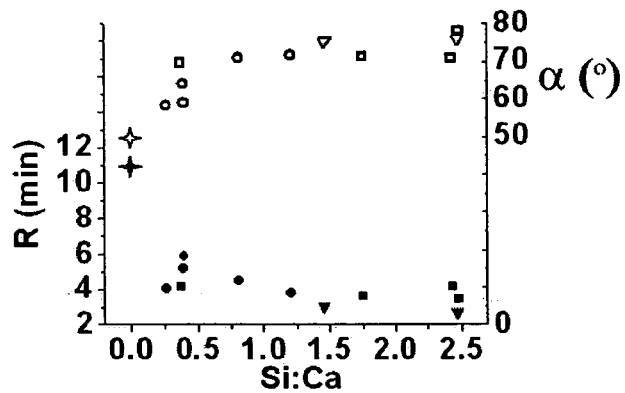
FIG. 19 is a plot of both clot detection time, R, (filled shapes) and rate of coagulation, α, (un-filled shapes) vs. BG Si:Ca. Data represents the mean of four trials. ■ Porous BG; ● Non-porous BG; ▼ Spherical BG.

The time until clot detection, R, decreases for increasing Si:Ca ratios in BG (FIG. 19). R is reduced by a factor of 2 when the Si:Ca ratio is doubled over the range studied. BG can perform the dual role of providing surface area for thrombosis and supplying $Ca^{2+}$ ions; hence there will be an optimum ratio of $SiO_2$ to $Ca^{2+}$ ions, which are co-factors throughout the clotting cascade, for the fastest hemostatic response. The BG induced coagulation rate, α, increases with increasing Si:Ca ratios and maximizes for the same Si:Ca ratio as for the minimum R time (Si:Ca($R_{min}α_{max}$) ~2.5). All blood clots induced by BGs resulted in stronger than natural clots, although there is no relationship between the ultimate clot strength and the ratio of Si:Ca in BG ($MA_{BG} \geq 62$ and $MA_{Natral}$=58 dyn/cm²).

Figure 20:
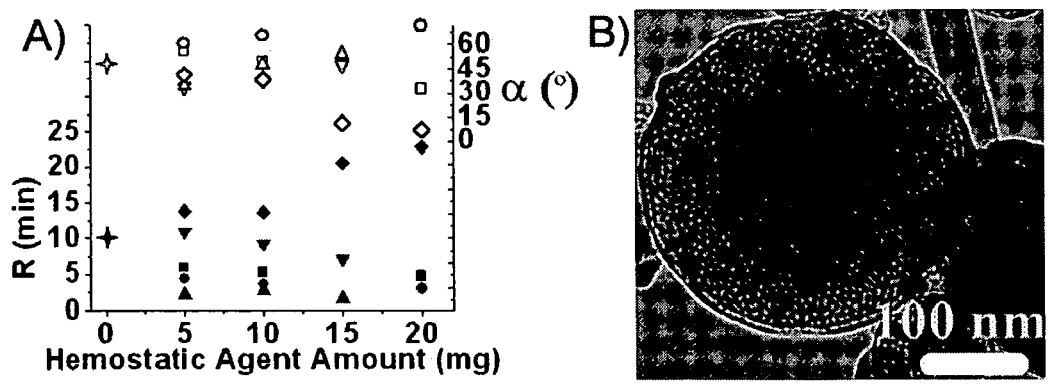
FIG. 20 shows: A) plot of both clot detection time, R, (filled shapes) and rate of coagulation, α, (un-filled shapes) vs. Si:Ca. Data represents the mean of four trials. ■ SBA-15 ● glass beads ▲ CaO ▼ $CaCO_3$ ◇ Hydroxylapatite; and B) TEM of Spherical BG.
Figure 21:
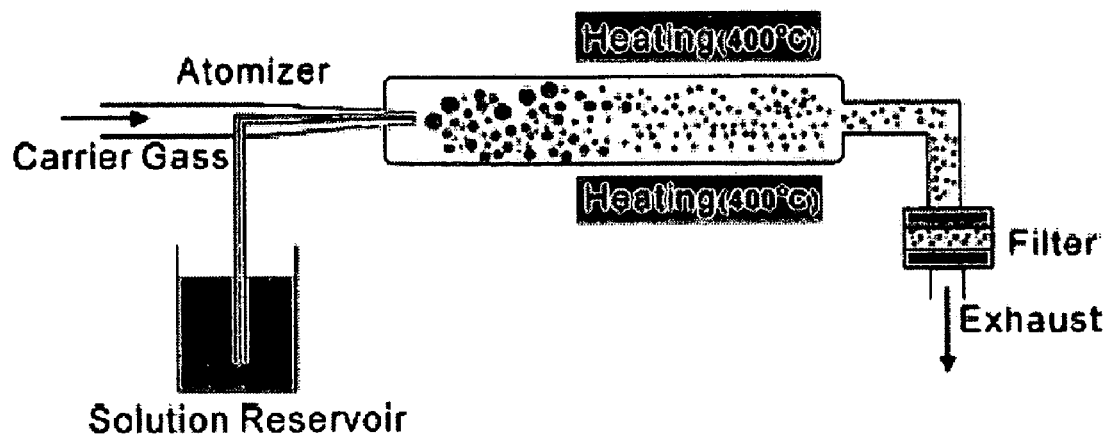
FIG. 21 is a diagram of a spray pyrolysis set-up.
Figure 22:
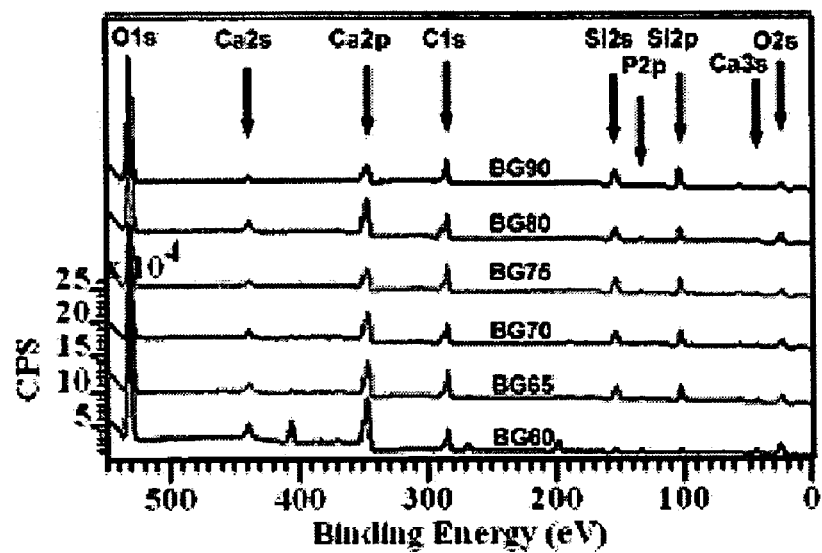
FIG. 22 shows XPS survey scans of porous bioactive glass.
Figure 23:
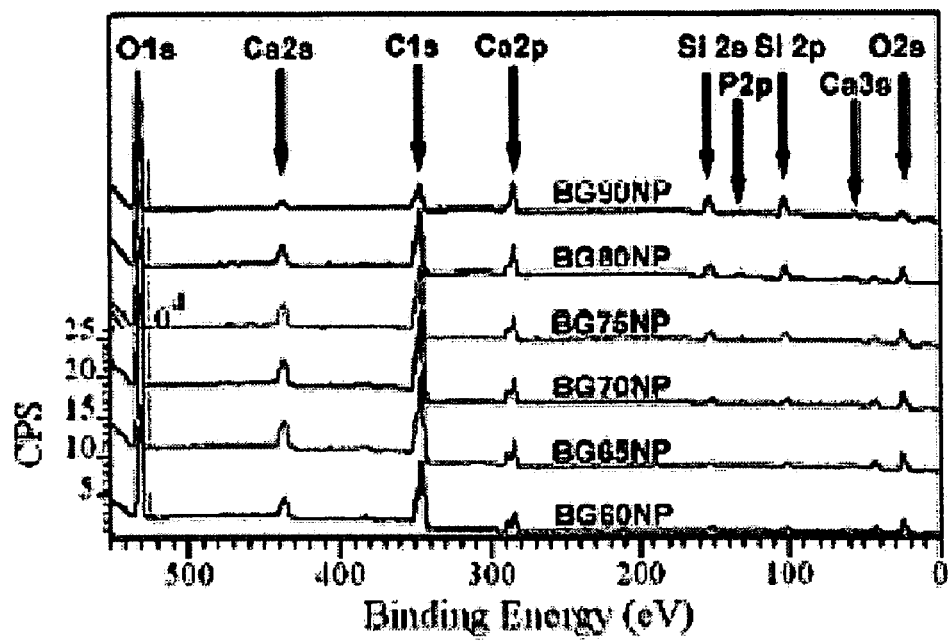
FIG. 23 shows XPS survey scans of non-porous bioactive glass.
Figure 24:
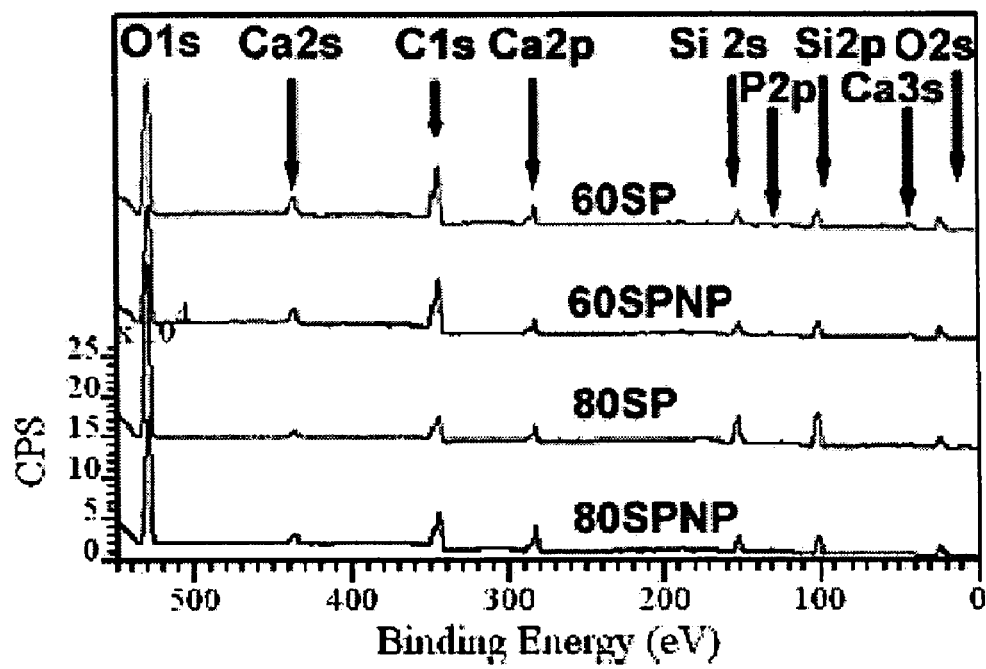
FIG. 24 shows XPS survey scans of spherical bioactive glass.
Figure 25:
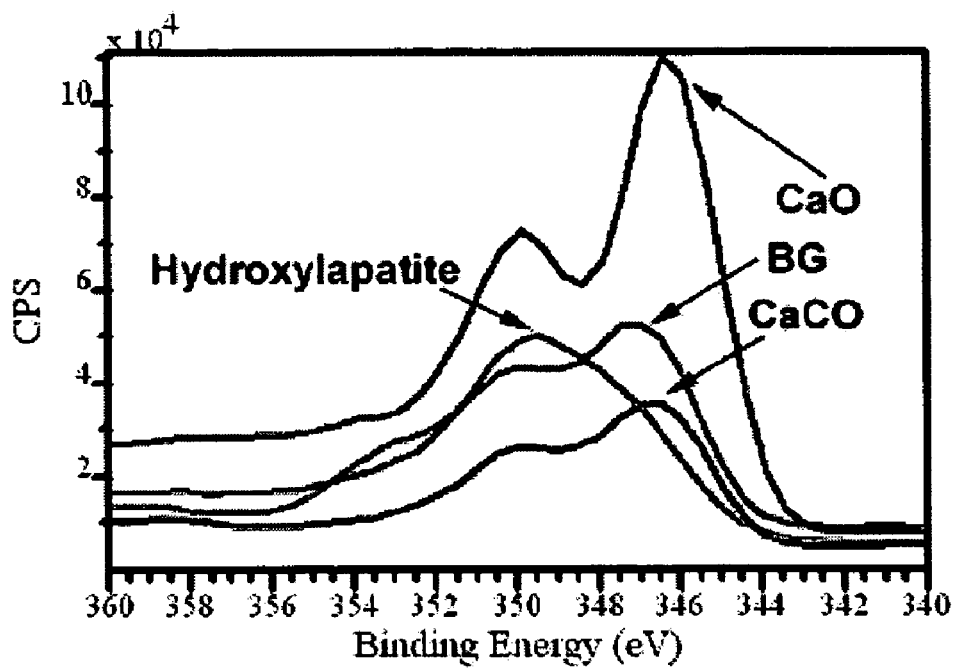
FIG. 25 shows a high-resolution XPS of Ca 2p binding energy in different HAs.
Figure 26:
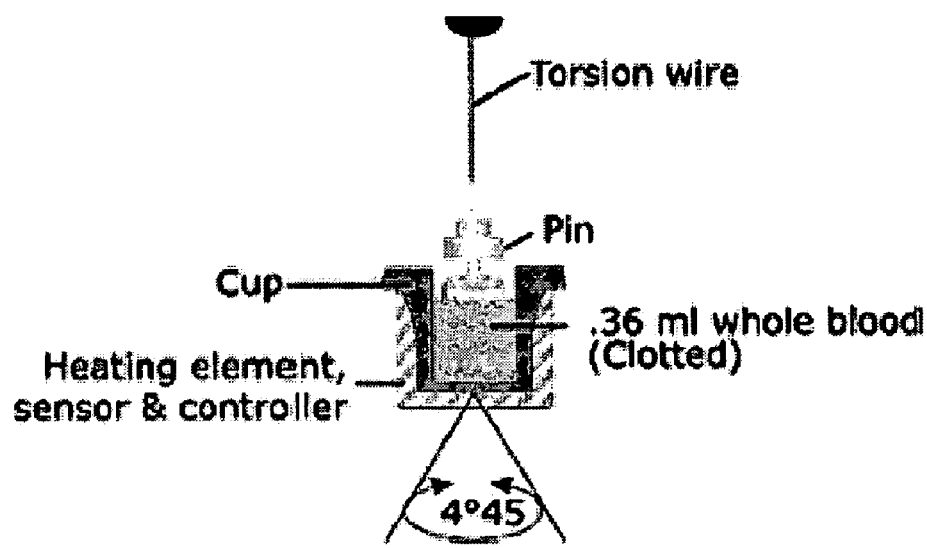
FIG. 26 is a diagram of a Thromboelastograph® sample cup.
Figure 27:
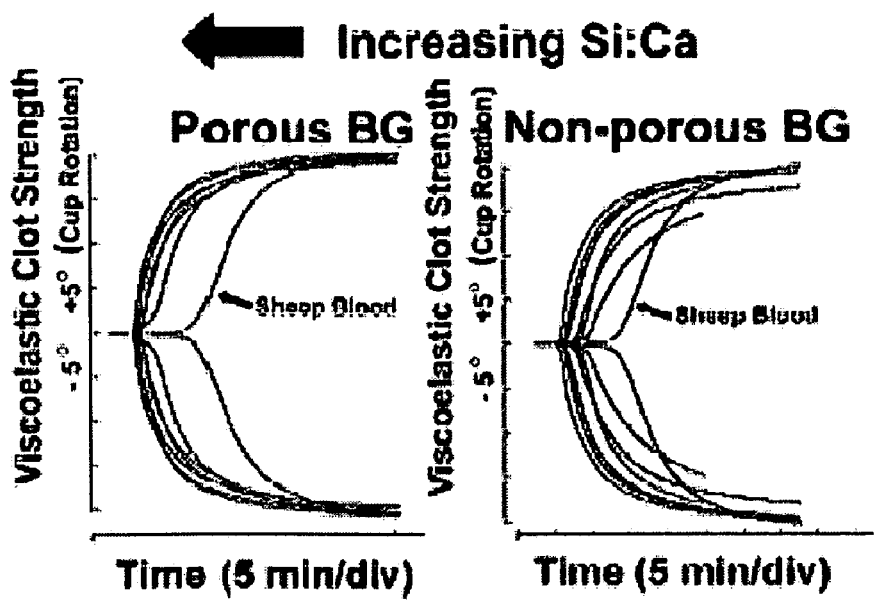
FIG. 27 is a thromboelastograph® plot of BG HAs. Inner Thromboelastograph plot on both plots is sheep blood without a HA added.
Figure 28:
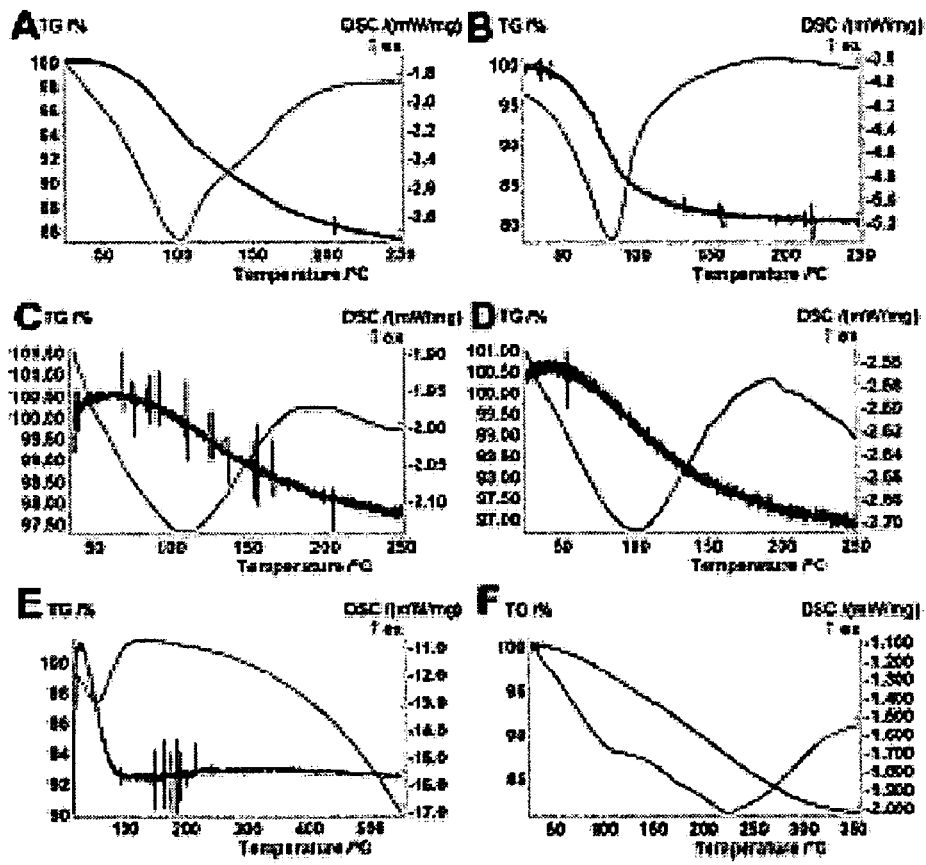
FIG. 28 shows TGA (black) and DSC (gray) of the desorption of water from saturated BG samples: A) PorousBG 80; B) Porous BG 80; C) Non-porous BG 60; D) Non-porous BG 80; E) SBA-15; F) QuikClot®.

The rational design of composite oxide HAs requires an understanding of the thrombotic effects of the constituent oxides individually as well as collectively. Towards this end, we have analyzed the in vitro hemostatic activity of porous $SiO_2$ (SBA-15; Zhao, D. et al., J. Am. Chem. Soc. 1998, 129, 6024) and CaO as model components of BG, as well as non-porous $SiO_2$ glass beads (Polyscience, Inc. Cat #07666), $CaCO_3$, and hydroxylapatite ($Ca_{10}(OH)_2(PO_4)_6$ Sigma Cat#289396) as related $SiO_2$ and Ca oxides. With the exception of hydroxylapatite, the oxide found in bone, each oxide demonstrated a reduced R time as more material was added to the blood (FIG. 20A). The reduced rate of coagulation, α, and clot strength, MA, associated with adding hydroxylapatite to blood are also evidence of its anti-thrombotic capacity. While there are several reports of organic based anticoagulants, hydroxylapatite represents a unique inorganic oxide that delays coagulation.

Despite a reduction in the clot initiation time, both the rate and ultimate clot strength decreased as more SBA-15 was mixed with blood. Although SBA-15 is a contact activator, due to its hydroxylated surface and ability to concentrate blood by dehydration, it appears to inhibit the propagation of clot formation. This concentrating effect might be 30 detrimental to clot propagation in the absence of sufficient $Ca^{2+}$ near the concentrated blood. Glass beads, which can provide an activating hydroxylated surface without dehydrating blood, demonstrate both accelerated α and increased MA in addition to reduced R as more material was added. The dehydration and concentration of blood by porous BG is not detrimental to clot propagation because of the $Ca^{2+}$ ions immediately near the concentrated blood. We have found that the inclusion of $Ca^{2+}$ ion sources into porous materials is beneficial to rapid clot formation, and $Ca^{2+}$ ions are co-factors that play a critical role in the immobilization and orientation of clotting enzymes on cellular surfaces by serving as the ionic bridge between two negatively charged residues (e.g. cellular surface and clotting factors). They ate consumed during thrombosis and fibrinolysis when Factor XIII cross-links fibrin with negatively charged glycosylated residues. It is reasonable to suggest that the faster rates of coagulation and stronger clots that can be attributed to both CaO and $CaCO_3$ are due in part to these agents' ability to present calcium to blood. CaO is far more soluble in blood (pH=7.4) than $CaCO_3$, and the greater total release of $Ca^{2+}$ ions may account for the ≧30% stronger clots induced by CaO than those resulting from any of the other oxides discussed in this teport($MA_{CaO}$=92 $MA_{OtheroxideHAsTested}$≦66. The difference in solubility between CaO and $CaCO_3$ appears negligible with regard to the rate of coagulation.

Un-dissolved calcium containing HA particles could interact with blood constituents (Jalilehvand, F., et al., *J. Am. Chem. Soc.* 2001, 123, 431); and high resolution x-ray photoelectron spectroscopic analysis demonstrates a lower Ca 2p binding energy for the more hemostatically active materials. Ca $2p_{3/2}$ in hydroxylapatite (349 eV) is 2 eV more than in BG, CaO, or $CaCO_3$ (347 eV), in agreement with previous work (Perez-Pariente, J. et al., *Chem. Mater* 2000, 12, 750; Koper, O. et al., *Chem. Mater* 1997, 9, 2468). Although the effect of the Ca environment is outlined for bone generating oxides (Lu, H. B. et al., *Anal. Chem.* 2000, 72, 2886), this is not the case for the related hemostatic trends.

We have observed that porous inorganic HAs have multiple acceleratory effects on blood coagulation, in conjunction with surface activation and control of local electrolytes, by concentrating blood and locally warming the surrounding tissue due to an exothermic $\Delta H_{Hydration}$ common to porous oxides. Although the original porous zeolite HA employed by the U.S. military is effective as a life-saving medical device, the excessive heat generation led to efforts to identify new materials that will be safer to apply and still be effective. The zeolite-based HAs typically released up to 700 J/g upon hydration, adsorb ~20% w/w $H_2O$, and have surface areas up to 700 $m^2/g$. Porous and non-porous BG release up to 400 J/g upon hydration, absorbed ~15% w/w $H_2O$, and have surface areas up to 400 $m^2/g$. The smaller $\Delta H_{Hydration}$ for BG HAs compared to zeolite-based HAs will still permit local dehydration of hemorrhaging blood without the excessive heat generated that tended to burn patients and inhibited the proper application of the HAs.

Preliminary results from studies of particle morphology indicate that size and shape ate key clotting parameters. By spray calcination of the BG precursor sol-gel, spherical BG can be produced (diam.=300 nm, pore size=5 nm) (FIG. 20B). Given similar Si:Ca ratios, spherical BG demonstrate reduced R times and faster a rates than irregular BG. Although both BG and zeolite HAs have high surface areas, the pore apertures (5mn, 4 Å respectively) limit interaction with larger biological media to the outermost particle surface. Spherical BG presents more of this available surface to blood than irregular BG. Research is on-going to further explore the hemostatic effect of increasing the surface to volume ratio as well as the role of surface roughness and charge.

Example 5

Antibacterial Activity of Ag-loaded Zeolite LT 5A Prepared by Ion Exchange and by Solid State Mixing In this example, the antibacterial activity of different formulations of Ag-loaded zeolite were compared. In method 1, QuikClot® (zeolite Linde type 5A) was ion exchanged with 10 solutions of varying concentrations of $AgNO_3$(aq). In method 2, solid-state mixing of $AgNO_3$:QuikClot® was achieved by mixing $AgNO_3$ and QuikClot® at 10% w/w $AgNO_3$, 1% w/w $AgNO_3$, 0.02% w/w $AgNO_3$, 0.01% w/w $AgNO_3$. All materials were ground w/mortar and pestle, pressed into pellets at 6 metric tons per cm. Samples were heated to 250° C. under vacuum to dehydrate and sterilize. The empirical formula was determined by X-ray photoelectron spectroscopy (XPS).

TABLE 9

XPS Characterization of Ag Loaded Zeolite A Samples Prepared

| — | Si | Al | O | Na | Ca | Ag | Empirical formula |
|---|---|---|---|---|---|---|---|
| QuikClot | 18.896 | 17.245 | 57.646 | 0.302 | 5.911 | 0 | Na0.299Ca5.85(SiO2)12(AlO2)12.H2O |
| F1 | 18.077 | 16.94 | 58.1 | 0.234 | 5.318 | 1.33 | Ag1.308Na0.230Ca5.230(SiO2)12(AlO2)12.H2O |
| F2 | 18.309 | 16.395 | 58.834 | 0.233 | 5.916 | 0.313 | Ag0.303Na0.2226Ca5.740(SiO2)12(AlO2)12.H2O |
| F3 | 18.549 | 16.893 | 58.053 | 0.316 | 5.814 | 0.376 | Ag0.366Na0.308Ca5.663(SiO2)12(AlO2)12.H2O |
| F4 | 18.528 | 16.951 | 58.101 | 0.293 | 5.922 | 0.206 | Ag0.200Na0.285Ca5.757(SiO2)12(AlO2)12.H2O |
| F5 | 19.482 | 17.784 | 56.605 | 0.262 | 5.709 | 0.157 | Ag0.159Na0.266Ca5.788(SiO2)12(AlO2)12.H2O |
| 100% AgNO3 | 0 | 0 | 0 | 0 | 0 | 100— | AgNO3 |
| F6 | 24.898 | 10.753 | 57.996 | 0.267 | 4.711 | 1.376 | Ag0.149Na0.290Ca5.110(SiO2)12(AlO2)12.H2O |
| F7 | 24.748 | 11.257 | 58.665 | 0.256 | 4.954 | 0.119 | Ag0.139Na0.299Ca5.781(SiO2)12(AlO2)12.H2O |

Figure 29:
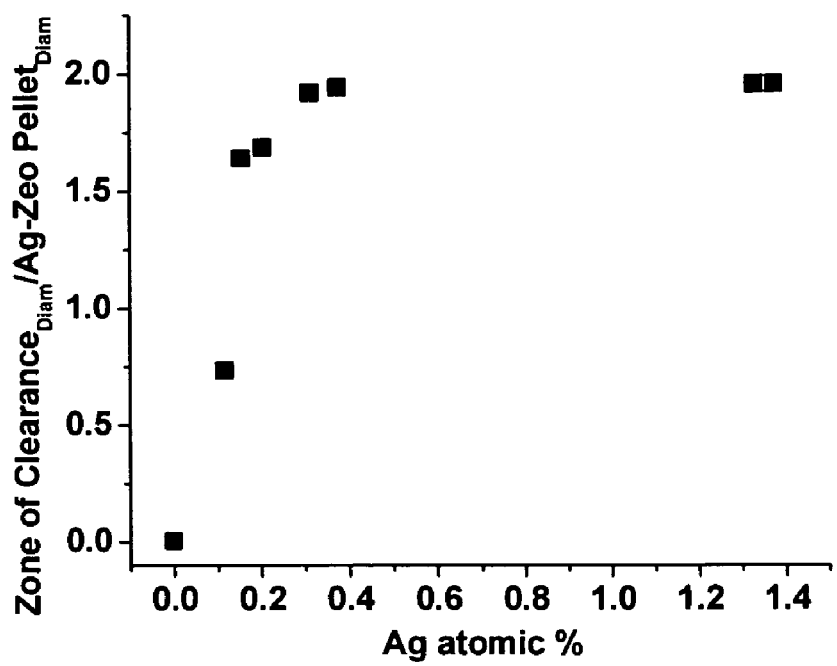
FIG. 29 shows antibiotic activity as a function of Ag content for ion exchange formulations of zeolite.
Figure 30:
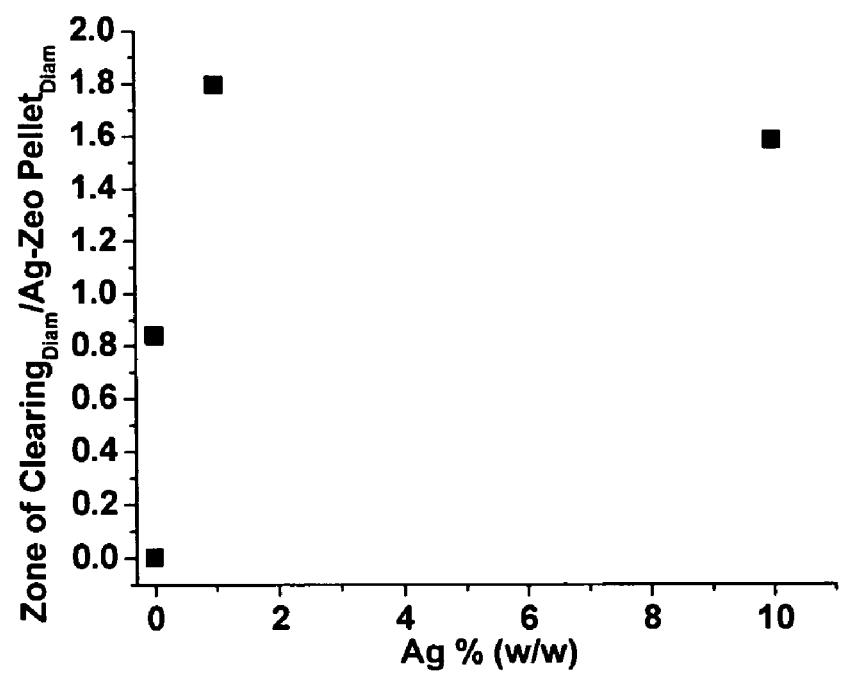
FIG. 30 shows antibiotic activity as a function of Ag content for solid state mixing formulations of zeolite.

Deposition and monitoring: Pellets, beads, and powders were deposited on LB Agar immediately after innoculated with *P. Aeruginosa*. Digital photographs were taken at 24, 48, and 72 hours of growth. Results are summarized in FIG. 29 and FIG. 30, for ion exchange and solid state mixing, respectively.

Formulations tested (in order of decreasing cost to add Ag)
$Ag_6Ca_3(SiO_2)_{12}(AlO_2)_{12}·27H_2O$ MW: 2655.417 g/mol
Ag=5.8 atomic %
A 3.5oz package of QuikClot®
Ion Exchange: Lowest Antibiotic Formulation without Reduced Antibiotic Effect After 24 hr
$Ag_{0.41}Ca_{5.796}(SiO_2)_{12}(AlO_2)_{12}·27H2O$
MW: 2135.947 g/mol; MW of Ag is 107.8682 g/mol
Ag=0.37 atomic %
Solid-State Mix: Lowest Antibiotic Formulation without Reduced Antibiotic Effect After 24 hr
1% w/w $AgNO_3$w/QuikClot®

Figure 31:
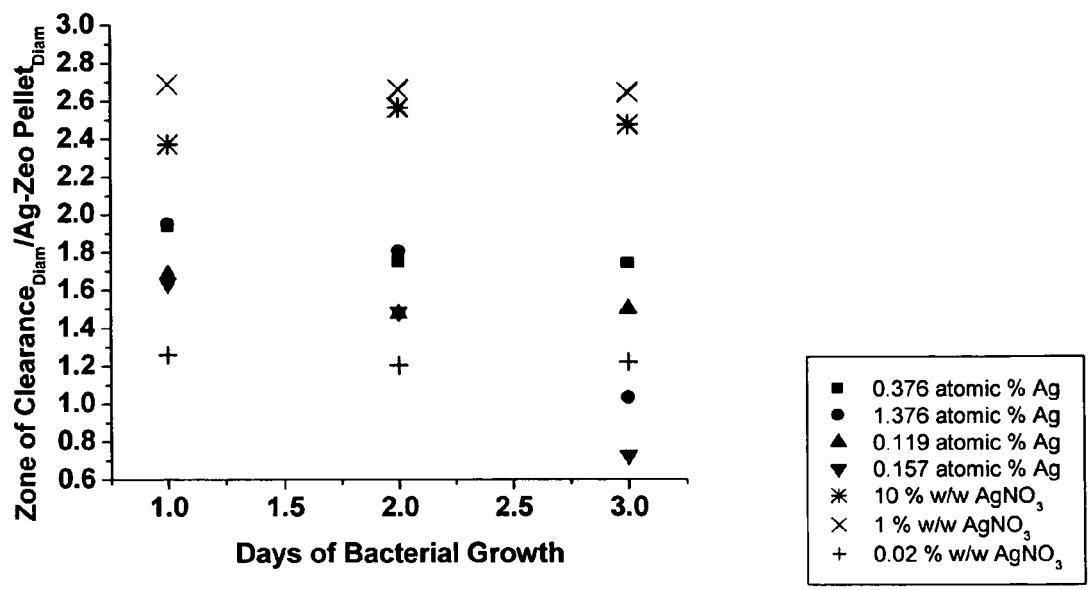
FIG. 31 shows size of zone of clearance per Ag-zeolite pellet size observed at 1, 2 and 3 days of bacterial growth.

Solid-state mixing works better for smaller granules than larger pellets. Ion exchange has better antibiotic activity after 24 hours. Comparisons were also made between 123A beads, 123J beads, 123A bead powder, 123J bead powder, Quik-Clot® powder, 123A powder, 123F beads and 123J powder. Powder makes better contact with bacteria than large beads. This helps with the diffusion and mass transport of $Ag^+$ ions Various formulations were deposited on LB Agar immediately after innoculated with *P. Aeruginosa*. Digital photos were taken at 24, 48, and 72 hours of growth. Results are summarized in FIG. 31. The following formulations were tested:

$Ag_{0.303}Na_{0.226}Ca_{5.740}(SiO_2)_{12}(AlO_2)_{12}.H_2O$
$Ag_{0.363}Na_{0.365}Ca_{5.636}(SiO_2)_{12}(AlO_2)_{12}.H_2O$
$Ag_{0.2}Na_{0.28}5Ca_{5.757}(SiO_2)_{12}(AlO_2)_{12}.HO$
$Ag_{0.159}Na0.266Ca_{5.788}(SiO_2)_{12}(AlO_2)_{12}.H_2O$
100% $AgNO_3$
10% $AgNO_3$ in QuikClot®
1% $AgNO_3$ in QuikClot®

Example 6

Diatomaceous Earth as a Hemostatic Agent

Figure 32:
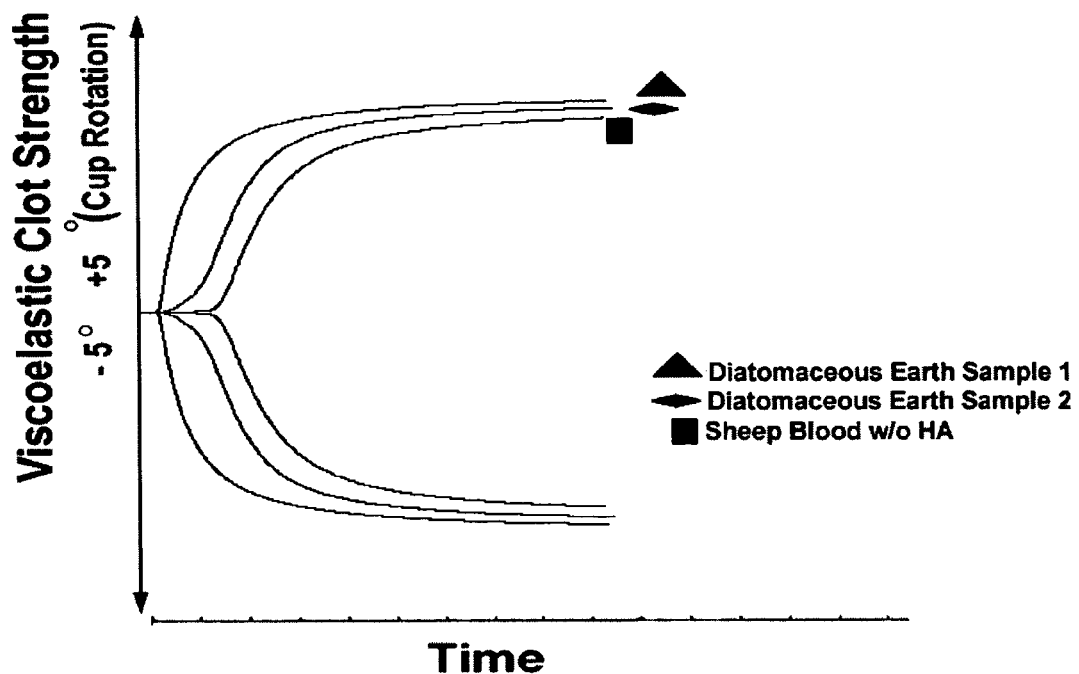
FIG. 32 is a Thromboelastograph® plot of the hemostatic activity of diatomaceous earth. Inner curve is sheep's blood without any agent added (square), second curve is 20 mg of a diatomaceous sample (PAW) (diamond), outermost curve is 20 mg of a diatomaceous sample (512) (triangle).

This example describes activation of clotting using diatomaceous earth as the hemostatic agent. Viscoelastic clot strength (cup rotation) was measured as a function of time for sheep's blood without hemostatic agent (HA) and with two different 20 mg samples of diatomaceous earth. The results are shown in the Thromboelastograph® plot depicted in FIG. 32. These data confirm that diatomaceous earth accelerates clotting as do the other hemostatic agents described herein.

From the foregoing it will be appreciated that, although specific embodiments of the invention have been described herein for purposes of illustration, various modifications may be made without deviating from the spirit and scope of the invention.

Throughout this application various publications are referenced. The disclosures of these publications in their entireties are hereby incorporated by reference into this application in order to more fully describe the state of the art to which this invention pertains.

What is claimed is:

1. A hemostatic composition for treating a bleeding wound comprising a hemostatically effective amount of a zeolite Linde type 5A, wherein the composition is produced to attenuate the heat of hydration of the composition by ion exchange and prehydration of the zeolite, wherein the zeolite is ion exchanged with $Ag^+$ ions, and wherein the zeolite is prehydrated from 1% to 3% by weight.

2. The composition of claim 1, wherein the zeolite has an internal surface area of 632 $m^2/g$ as measured by BET $N_2$ adsorption.

3. The composition of claim 2, wherein the zeolite has an internal surface area of 723 $m^2/g$ as measured by BET $N_2$ adsorption.

4. The composition of claim 1, wherein the zeolite has a loading of $Ag^+$ ions of at least 0.2 atomic % as determined by X-ray photoelectron spectroscopy.

5. The composition of claim 1, wherein the zeolite is ion-exchanged with 0.1M to 1M aqueous solutions.

6. The composition of claim 5, wherein the aqueous solution comprises silver nitrate.

7. The composition of claim 1, wherein the zeolite comprises $Na_{0.5}Ca_{5.75}(SiO_2)_{12}(AlO_2)_{12}$.

8. The composition of claim 1, wherein the zeolite is prehydrated 3% by weight.

9. The composition of claim 1, wherein the zeolite is prehydrated 1% by weight.

10. The composition of claim 1, wherein the composition has a heat of hydration of 212 J/g or less.

11. The composition of claim 10, wherein the composition has a heat of hydration of 111 J/g or less.

12. The composition of claim 1, wherein the composition has a time to initiate clot formation (R), as measured by thromboelastography, of 1.8 minutes or less.

13. The composition of claim 12, wherein the composition has a time to initiate clot formation (R), as measured by thromboelastography, of 0.9 minutes or less.

14. The composition of claim 1, comprising a biologically active agent attached to a surface of the zeolite.

15. The composition of claim 14, wherein the biologically active agent comprises a clot promoting reactant.

16. The composition of claim 15, wherein the clot promoting reactant comprises thrombin.

17. The composition of claim 1, comprising an inorganic salt.

18. The composition of claim 17, wherein the inorganic salt comprises silver, zinc, copper, magnesium, calcium, or nickel.

19. The composition of claim 17, wherein the inorganic salt is CaO, $CaCl_2$, $AgNO_3$, $Ca(NO_3)_2$, $Mg(NO_3)_2$, $Zn(NO_3)_2$, $NH_4NO_3$, AgCl, $Ag_2O$, zinc acetate, magnesium acetate, calcium citrate, zinc citrate, magnesium citrate, calcium acetate, calcium phosphate, or aluminum sulfate.

20. The composition of claim 17, wherein the composition has a loading of $AgNO_3$ of at least 0.01% by weight as provided via solid state mixing.

* * * * *